(12) United States Patent
Orvis et al.

(10) Patent No.: US 10,893,816 B2
(45) Date of Patent: Jan. 19, 2021

(54) PREDICTIVELY CONTROLLING OPERATIONAL STATES OF WEARABLE DEVICE AND RELATED METHODS AND SYSTEMS

(71) Applicant: Caeden, Inc., New York, NY (US)

(72) Inventors: Skip Thomas Orvis, Murphys, CA (US); Nora Elam Levinson, Washington, DC (US); Jamal Eddine Mouline, Durham, NC (US)

(73) Assignee: CAEDEN, INC., New York, NY (US)

( * ) Notice: Subject to any disclaimer, the term of this patent is extended or adjusted under 35 U.S.C. 154(b) by 0 days.

(21) Appl. No.: 16/457,551

(22) Filed: Jun. 28, 2019

(65) Prior Publication Data
US 2019/0336009 A1 Nov. 7, 2019

Related U.S. Application Data

(63) Continuation of application No. PCT/US2017/068945, filed on Dec. 29, 2017.
(Continued)

(51) Int. Cl.
*A61B 5/0205* (2006.01)
*A61B 5/024* (2006.01)
(Continued)

(52) U.S. Cl.
CPC ........ *A61B 5/02438* (2013.01); *A61B 5/0004* (2013.01); *A61B 5/0006* (2013.01);
(Continued)

(58) Field of Classification Search
CPC ........ G06F 3/0304; G06F 1/163; G06F 3/011; A61B 5/02438; A61B 5/486; A61B 5/4866; A61B 5/7264; A61B 5/7278; A61B 5/7405; A61B 5/742; A61B 5/7455; A61B 5/0205; A61B 5/0816; A61B 5/087; A61B 5/6823; A61B 5/02405; A61B 5/0006;
(Continued)

(56) References Cited

U.S. PATENT DOCUMENTS 7,641,618 B2   1/2010 Noda et al.
2005/0124906 A1*  6/2005 Childre ................ A61B 5/0816
                                                       600/529
(Continued)

FOREIGN PATENT DOCUMENTS

CN          105797257 A       7/2016

OTHER PUBLICATIONS

Keytel et al., "Prediction of energy expenditure from heart rate monitoring during submaximal exercise," Journal of Sports Sciences, Mar. 1, 2005, 46 pages.
(Continued)

*Primary Examiner* — An T Nguyen
(74) *Attorney, Agent, or Firm* — Zilka-Kotab, P.C.

(57) ABSTRACT

A method for predictively controlling an operational state of a wearable device, according to one embodiment, includes collecting historical sensor data acquired by one or more sensors of a wearable device. The historical sensor data is analyzed for detecting a pattern therein. A time to change an operational state of the wearable device is predicted based on the analysis. The change of the operational state is instructed at the predicted time.

15 Claims, 15 Drawing Sheets

Related U.S. Application Data

(60) Provisional application No. 62/440,368, filed on Dec. 29, 2016, provisional application No. 62/440,359, filed on Dec. 29, 2016, provisional application No. 62/440,362, filed on Dec. 29, 2016, provisional application No. 62/440,340, filed on Dec. 29, 2016, provisional application No. 62/440,351, filed on Dec. 29, 2016, provisional application No. 62/440,356, filed on Dec. 29, 2016, provisional application No. 62/440,363, filed on Dec. 29, 2016.

(51) Int. Cl.
| | | |
|---|---|---|
| *G06F 3/03* | (2006.01) | |
| *A61B 5/00* | (2006.01) | |
| *A61B 5/08* | (2006.01) | |
| *A61B 5/087* | (2006.01) | |
| *G04G 17/04* | (2006.01) | |
| *G06F 1/16* | (2006.01) | |
| *G06F 3/01* | (2006.01) | |
| *G06K 9/00* | (2006.01) | |
| *A61B 5/0245* | (2006.01) | |

(52) U.S. Cl.
CPC .......... *A61B 5/0022* (2013.01); *A61B 5/0205* (2013.01); *A61B 5/02405* (2013.01); *A61B 5/087* (2013.01); *A61B 5/0816* (2013.01); *A61B 5/486* (2013.01); *A61B 5/4866* (2013.01); *A61B 5/6823* (2013.01); *A61B 5/725* (2013.01); *A61B 5/7264* (2013.01); *A61B 5/7278* (2013.01); *A61B 5/742* (2013.01); *A61B 5/7405* (2013.01); *A61B 5/746* (2013.01); *A61B 5/7455* (2013.01); *G04G 17/04* (2013.01); *G06F 1/163* (2013.01); *G06F 3/011* (2013.01); *G06F 3/0304* (2013.01); *G06K 9/00892* (2013.01); *A61B 5/0245* (2013.01); *A61B 5/02416* (2013.01); *A61B 5/02433* (2013.01); *A61B 5/6824* (2013.01); *A61B 2560/0247* (2013.01); *G06K 2009/00939* (2013.01)

(58) Field of Classification Search
CPC ..... A61B 5/746; A61B 5/0004; A61B 5/0022; A61B 5/725; A61B 5/02416; A61B 5/6824; A61B 2560/0247; A61B 5/02433; A61B 5/0245; G06K 9/00892; G06K 2009/00939; G04G 17/04
See application file for complete search history.

(56) References Cited

U.S. PATENT DOCUMENTS

| | | | |
|---|---|---|---|
| 2009/0012387 A1 | 1/2009 | Hanson et al. | |
| 2010/0298730 A1 | 11/2010 | Tarassenko et al. | |
| 2011/0066062 A1 | 3/2011 | Banet et al. | |
| 2015/0182130 A1* | 7/2015 | Utter, II | A61B 5/681 600/483 |
| 2016/0023047 A1 | 1/2016 | Wisbey et al. | |
| 2017/0056722 A1* | 3/2017 | Singh | G06F 1/26 |
| 2017/0135633 A1* | 5/2017 | Connor | A61N 1/36557 |
| 2018/0140254 A1* | 5/2018 | Kubo | A61B 5/6803 |
| 2018/0307314 A1* | 10/2018 | Connor | G01R 27/02 |
| 2019/0006030 A1* | 1/2019 | Mullin | G16H 40/20 |
| 2019/0059822 A1* | 2/2019 | Wang | A61B 5/1102 |
| 2019/0336009 A1* | 11/2019 | Orvis | A61B 5/0816 |
| 2019/0371342 A1* | 12/2019 | Tukka | H04M 1/72519 |

OTHER PUBLICATIONS

Daley, J., "Heart Rate Based Calorie Burn Calculator," Shapesense, 2019, 10 pages, retrieved from http://www.shapesense.com/fitness-exercise/calculators/heart-rate-based-calorie-burn-calculator.shtml.
Wicks et al., "HR Index—A Simple Method for the Prediction of Oxygen Uptake," Medicine & Science in Sports & Exercise, vol. 43, Issue. 10, Oct. 2011, pp. 2005-2012.
Ashley et al., "Conquering the ECG," In Cardiology Explained (Ch.3), Remedica, 2004, 34 pages, retrieved from https://www.ncbi.nlm.nih.gov/books/NBK2214/.
International Search Report and Written Opinion from PCT Application No. PCT/US2017/068945, dated Jun. 19, 2018.

\* cited by examiner

PREDICTIVELY CONTROLLING OPERATIONAL STATES OF WEARABLE DEVICE AND RELATED METHODS AND SYSTEMS

FIELD OF THE INVENTION

The present invention relates to wearable devices, and more particularly, this invention relates to wearable devices, processes for use with wearable devices, and/or related systems and methods.

BACKGROUND

Wearable devices are becoming very popular. However, existing wearable devices and system with which they communicate have limited capabilities, and moreover, lack intelligence to work with imperfect data, such as erroneous steps, varying heart rate, and sensor-related values affected by changing variables such as motion artifacts, lighting conditions, user skin tones, etc.

SUMMARY

A method for predictively controlling an operational state of a wearable device, according to one embodiment, includes collecting historical sensor data acquired by one or more sensors of a wearable device. The historical sensor data is analyzed for detecting a pattern therein. A time to change an operational state of the wearable device is predicted based on the analysis. The change of the operational state is instructed at the predicted time.

A computer program product according to one embodiment, includes a nontransitory computer readable medium having program instructions embodied therewith, the program instructions executable by a computer to cause the computer to perform the foregoing method.

A system, according to one embodiment, includes a processor and logic integrated with the processor, executable by the processor, or integrated with and executable by the processor. The logic is configured to perform the foregoing method.

Other aspects and advantages of the present invention will become apparent from the following detailed description, which, when taken in conjunction with the drawings, illustrate by way of example the principles of the invention.

DETAILED DESCRIPTION

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

The following description discloses several preferred embodiments of wearable devices, processes for use with wearable devices, and/or related systems and methods. Various descriptions of a wearable device, a sensor system, a data processing and communications link as well as the use of mathematical formulae to act upon a data set that includes imperfect data to correlate that data into usable information for a user may be applicable to any of the various embodiments listed below.

Illustrative System Architecture

Figure 1:
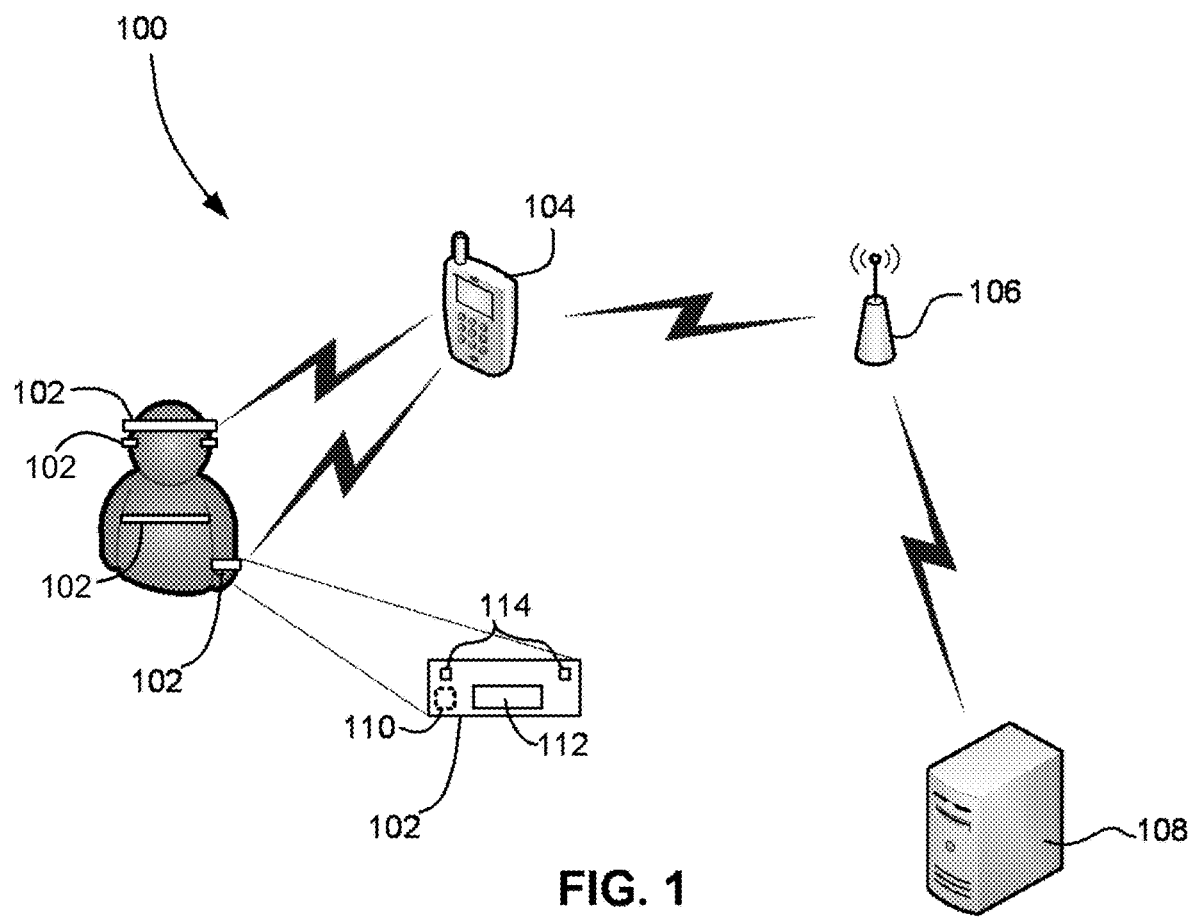
FIG. 1 depicts an architecture of an illustrative system, in accordance with one embodiment.

FIG. 1 depicts an architecture of an illustrative system 100, in accordance with one embodiment. As an option, the present system 100 may be implemented in conjunction with features from any other embodiment listed herein, such as those described with reference to the other FIGS. Of course, however, such system 100 and others presented herein may be used in various applications and/or in permutations which may or may not be specifically described in the illustrative embodiments listed herein. Further, the system 100 presented herein may be used in any desired environment.

The system 100 includes at least one wearable device 102, and in the example shown, includes two wearable devices 102. The wearable devices 102 are shown being worn on a user. Each wearable device 102 may include a subsystem 110, a user interface element 112, one or more sensors 114, etc.

The system 100 may include a host device, referred to herein as a host 104. The host 104 may be any type of device that can communicate with a wearable device 102, such as a mobile phone, tablet, laptop, etc. The host 104 may be in communication with a remote server 108 via a network 106 of any type. The remote server 108 may provide any desired functionality, such as host a website, interface with or manage a cloud service such as cloud storage, maintain a database, etc.

In some approaches, one or more of the wearable devices 102 may connect directly to a network 106 to communicate with a remote server 108, a host 104, etc.

More information about various components of the system 100 is presented below.

Wearable Device

A wearable device, according to various embodiments, may include an electromechanical and/or electrochemical system that can be made up of subsystems comprised of items such as printed circuit boards having processing circuits, batteries, wired and/or connector-based interconnects, user interface elements that can generate mechanical, electrical, visual or a combination of these stimuli to notify the user of actions or states of operation and/or alert users to notifications of items related to the operation of the system. Such wearable devices may also include communication elements such as radios, infrared or other line of sight, and/or electromagnetic communications systems for such things as unidirectional and/or bidirectional communications.

A wearable device may include other input elements such as buttons, switches, gyroscopic and/or other motion based sensors, environmental sensors that can include optical, thermal, moisture sensitive and/or electrochemical based elements.

In addition to the above features, a wearable device may have various self-stimulating, transmitter/receiver pairs. These can be items that are based in the same physical realm such as an optical and/or infrared output with an optical and/or infrared receiver, for example Photoplethysmography (PPG). They may also include other stimuli sensor pair such as Electroencephalogram (EEG) and/or via other methods such as Skin Conductance Response also known as Galvanic Skin Response (GSV) and Electro-dermal Activity (EDA).

A wearable device can be worn at some location on or near the body with direct contact between the device and the user, or with some space therebetween, such as due to the presence of clothing therebetween. Illustrative locations on which a wearable device may be worn include any of: the head, neck, ears, upper and lower arms, wrists, hands, fingers, palms, chest, back, waist, upper and lower legs and upper and lower surfaces of the feet.

Wearable devices may take the form of bracelets, armbands, fabric straps, necklaces, earphones, hats, headbands, sleeves, shoes, socks, gloves and/or other articles of clothing, depending on the intended use and/or intended body placement. For example, some wearable devices may have rubbery or elastic components, e.g., as in a strap or elastic headband.

Wearable devices according to various embodiments may include any combination of the features presented herein. For example, a particular embodiment of a wearable device may include selected ones of the features presented herein, while another embodiment of a wearable device may include a different set of any of the features presented herein.

Similarly, a host for communicating with a mobile device may include any combination of host-side features presented herein. Likewise, a system comprising a host and a wearable device or devices may include any combination of the features presented herein.

Accordingly, recitation of particular configurations herein should be considered exemplary only and not limiting in any way.

Sensor System

A wearable device and/or host may include one or more sensors of any known type. Some sensors are able to capture biometrics and output biometric data. Illustrative types of sensors are listed above in the description of a wearable device. Other types of sensors may include temperature sensors, humidity sensors, altitude sensors, oxygen sensors, motion sensors, positional sensors (e.g., GPS sensor), etc. The sensors may be present individually, in an array, etc. Preferably, the sensors are positioned toward an outer side of the device to which they are coupled, e.g., in a location most likely to enable the sensor to capture the condition to be sensed.

The sensors may be connected electrically to a main circuit board of the device to which coupled, and/or may be assembled into sub-systems which connect to the device through wired and/or wireless connections. In other approaches, the sensor may be mounted on one device, e.g., a wearable device, and communicate to another device, e.g., a host through wired and/or wireless connections.

In use, the sensors may be used one at a time and/or may dynamically cycle through multiples used at a time to create sensor arrays. The sensor's data may be conveyed via a direct electrical signal in standard formats such as I2C, PDM, SPI, a proprietary signal format between the sensor and the main or several system coprocessors, etc. For wireless connections, any known technique may be used. Exemplary wireless communications techniques are presented in the next section. For sensors coupled to a wearable device but communicate directly to a host, such sensors may be considered part of the wearable device, and therefore communications between the sensor and host may be described herein as between the wearable device and host.

Data Processing and Communications Link

The processor operating on the data may perform real-time processing as the data comes in from the sensors and/or the data may be stored into memory for fetching and processing at a later time. The processor or processors may be local to the wearable device, on a connected local host which is connected to the wearable device and/or sensor via a wired cable or connector and/or wirelessly via a wireless connection, e.g., one using a wireless standard such as Proprietary Sub-GHz, Wi-Fi (b,g,n), Bluetooth, Bluetooth Low Energy, ZigBee, Z-Wave, Thread and/or other wireless network or link.

The data may be streamed in native form, in processed form, in compressed form, etc. from the wearable device directly or indirectly to a cloud based server and processing system and/or to the server and processing system after passing through the connected local host device. In one approach, transmission of data from the local host device to the cloud based server and/or processing system can be over similar wireless protocols as mentioned previously. In another approach, the host may be connected to the remove server via a wired networking connection such as a proprietary wired data network, Ethernet, optical, another data transmission link, etc.

Data Storage

A wearable device may, in some approaches, have, or have access to, onboard, remote (e.g., host based) and/or cloud based memory. Especially when simultaneous input is being collected from multiple sensors, storage of the sensor data may provide more time for the involved microprocessors to act upon the sensor data without the data being lost due to system resource constraints.

Any data received from and/or derived from sensors may be "sensor data" as used herein. The data collected from the sensors can be stored in its native, raw, format with all bits intact and/or it may be compressed on the wearable device. Compression is particularly useful for transmission of the data across a data link. A combination of native data storage and compressed data storage may be instituted to optimize both processing time as well as local and/or remote data storage capacity requirements. Additional considerations may be made to ensure that the data synchronization (sync) time between the wearable and a connected host and/or cloud services system has been optimized to the benefit of the system resource allocation as well as the user experience for the end user of the device.

An advanced wearable device according to one embodiment is configured to prioritize and utilize both RAM (Random Access Memory) as well as nonvolatile memory (e.g., NAND flash memory) to temporarily and more permanently store data that the sensors have captured.

Imperfect Data Correction

As the data is collected from the sensors and stored and/or processed in its native and/or compressed form, data inaccuracies may be inherent to the overall system. Through development of spectral analysis algorithms with a foundation in portions of widely accepted least-squares principles similar to Fourier analysis such as computational results found through the work of Lomb, Vanicek and Scargle, such imperfect data may be corrected to enable use of the data.

A method for detecting resonance breathing may include an algorithmic implementation to detect resonance breathing in a wearable system in the absence of perfect data.

Using a wearable device that may be positioned at some location on the user's body, e.g., wrist, ear, chest, neck or otherwise, to collect imperfect sensor data using one or more sensors, such data may be processed to detect and report breathing resonance. The data may be processed on the device itself, on a connected remote host processor, and/or on a cloud based data backend server.

Figure 2:
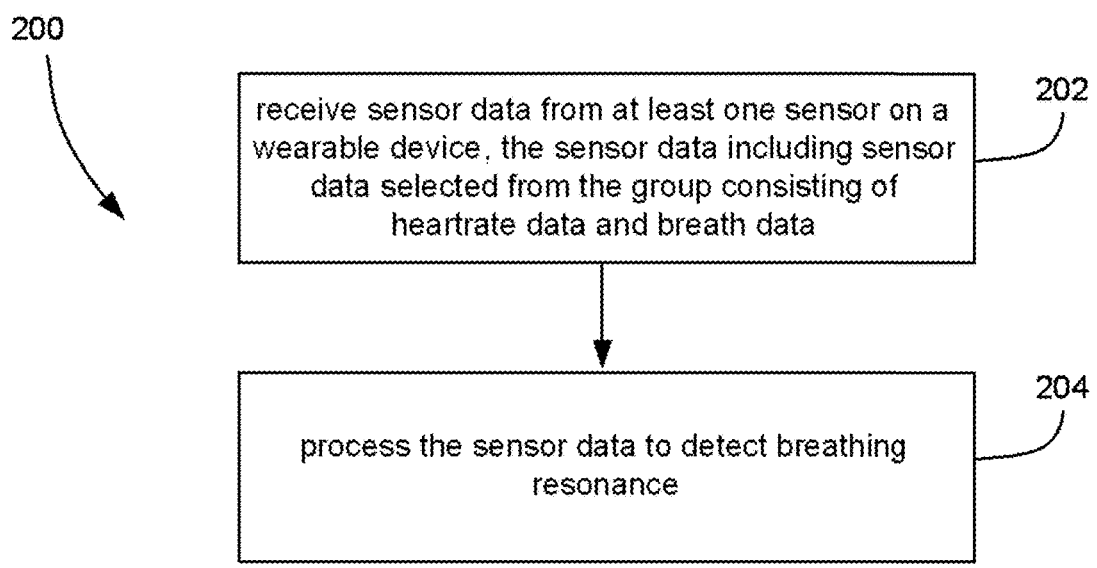
FIG. 2 is a flowchart of a method for detecting resonance breathing in accordance with one embodiment.

FIG. 2 shows a method 200 for detecting resonance breathing in accordance with one embodiment. As an option, the present method 200 may be implemented in conjunction with any other the other processes and features such as those shown in the other FIGS. described herein. Further, the methods presented herein may be carried out in any desired environment. Moreover, more or less operations than those shown in FIG. 200 may be included in method 200, according to various embodiments. It should again be noted that any of the features described in the present disclosure may be used in any of the embodiments described in accordance with the various methods.

Operation 202 includes receiving sensor data from at least one sensor on a wearable device, the sensor data including sensor data selected from the group consisting of heartrate data and breath data. Operation 204 includes processing the sensor data to detect breathing resonance.

Figure 3:
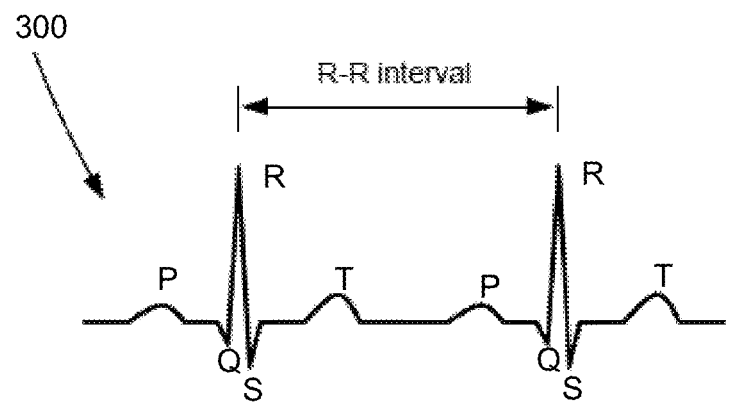
FIG. 3 is a graphical signal of a heart rate wave form with the R-R interval annotated.

In order to detect a resonant state, various signal processing techniques may be used on a time-ordered stream of R wave peak to R wave peak (R-R) intervals. FIG. 3 is a graphical signal of a heart rate wave form 300 with the R-R interval annotated. The P wave is a small deflection wave that represents atrial depolarization. The three waves of the QRS complex represent ventricular depolarization. For the inexperienced, one of the most confusing aspects of ECG reading is the labeling of these waves. If the wave immediately after the P wave is an upward deflection, it is an R wave; if it is a downward deflection, it is a Q wave. Small Q waves tend to correspond to depolarization of the interventricular septum. Q waves can also relate to breathing and are generally small and thin. They can also signal an old myocardial infarction, in which case they tend to be larger and wider. The R wave reflects depolarization of the main mass of the ventricles; hence it is the largest wave. The S wave signifies the final depolarization of the ventricles, at the base of the heart. The ST segment, which is also known as the ST interval, is the time between the end of the QRS complex and the start of the T wave. It reflects the period of zero potential between ventricular depolarization and repolarization. T waves represent ventricular repolarization (atrial repolarization is obscured by the large QRS complex).

Fast Fourier Transform (FFT) is the signal processing gold standard, but it may be unsuitable for this use case as it requires an evenly spaced series of data. While interpolation techniques can be used to fill in the gaps, a preferred approach uses a technique that allows for non-uniform time series data. One of these techniques is the Lomb-Scargle periodogram which is a least squares spectral analysis technique that performs well in situations where the signal is uneven and/or missing data.

In one approach, the algorithm takes input data from the sensor subsystems to identify a user's resonant frequency. When a person breathes at a certain cadence, $R_B$, measured in "breaths per minute", their heart rate peaks (HR) will begin to oscillate at a specific frequency, called the Resonant Frequency ($F_R$), calculated by:

$$F_R = \frac{R_B}{60}$$

Resonant breathing is a paced breathing technique whereby a person breathes at a certain frequency to incite a physiological response within their body. This physiological response causes the person's instantaneous HR (R-R-Interval) to oscillate in sync with their breathing. As such the equation above applies across both heartrate sensor data analysis as well as breath sensor data. Accordingly, heartrate and/or breath sensor data may be used.

To detect resonance, a normalized Lomb-Scargle spectrogram may be generated from a trailing section of data ($T_S$ seconds from the current time, where the value of $T_S$ may be predefined, retrieved from a database, etc.). If there is a significant portion of power concentrated around the resonant frequency, then the person is said to be in a resonant state.

Figure 4:
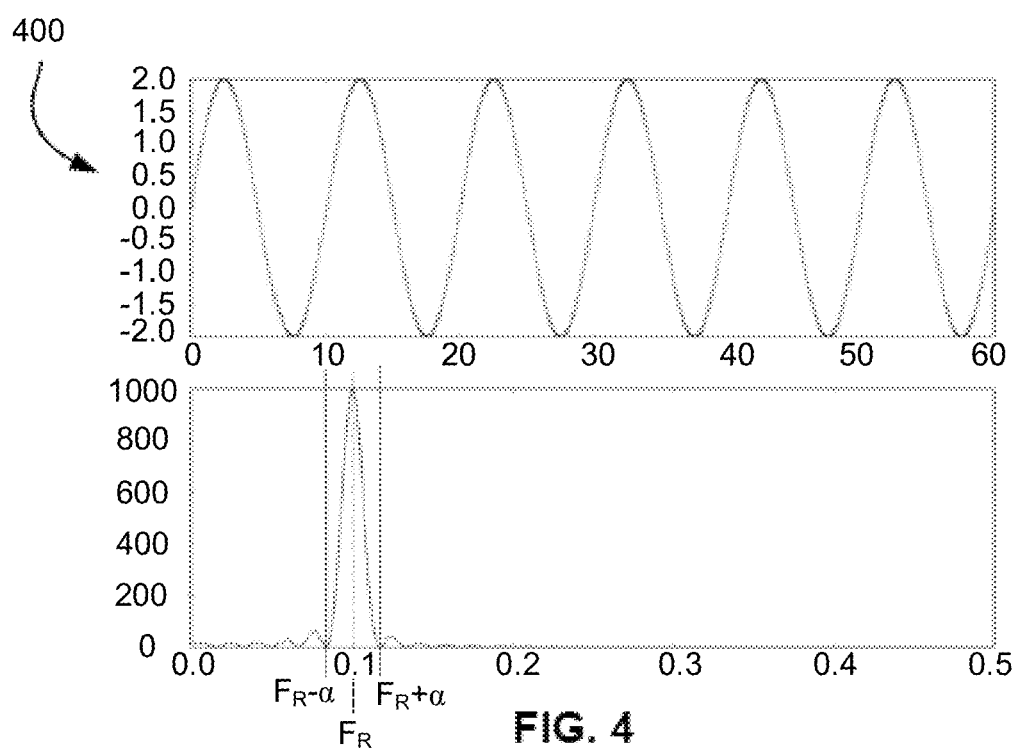
FIG. 4 is a graph of a simulated R-R Interval series of a heart beat in a resonance state.

FIG. 4 is a graph 400 of a simulated R-R Interval series of a heart beat in a resonance state. In this case $R_B=6$, and $F_R=0.1$ hz. The top graph represents the original signal, and the bottom graph is a representation of the Lomb-Scargle periodogram computed using conventional techniques.

A window around $F_R$, designated by α, is chosen in order to assess the concentration of power. Resonant Power ($P_R$) for some spectrogram S(f) is then defined as:

$$P_R \Sigma_{i=F_R-\alpha}^{2\alpha} S(i)$$

Total Power ($P_T$) is defined as:

$$P_T = \Sigma_{i+0}^{Pmax} S(i)$$

An R-R-Interval signal is then said to be resonant if the percentage of power within the window is within a predefined range, such as greater than some cutoff percentage C:

$$R = \frac{P_R}{P_T} > C$$

Known data filtering techniques may be used to eliminate data based on various conditions such as low quality data, and data that is determined to have been taken when the user's body parameters are out of predetermined bounds for the specific measurement (such as too active). Moreover, data filtering to exclude data may include identifying whether or not the data has been corrupted by external factors such as heat, sweat, external light, the ambient temperature, user skin surface temperature, the time of day, location of the user during the data collection, etc. Data from other sensors on the wearable device and/or host may be used to derive information about such conditions.

The particular variables that are input into the pre-filtering and resonance detection algorithms may be selected by one skilled in the art according to the algorithms used, based upon the math and information included in this section.

Figure 5:
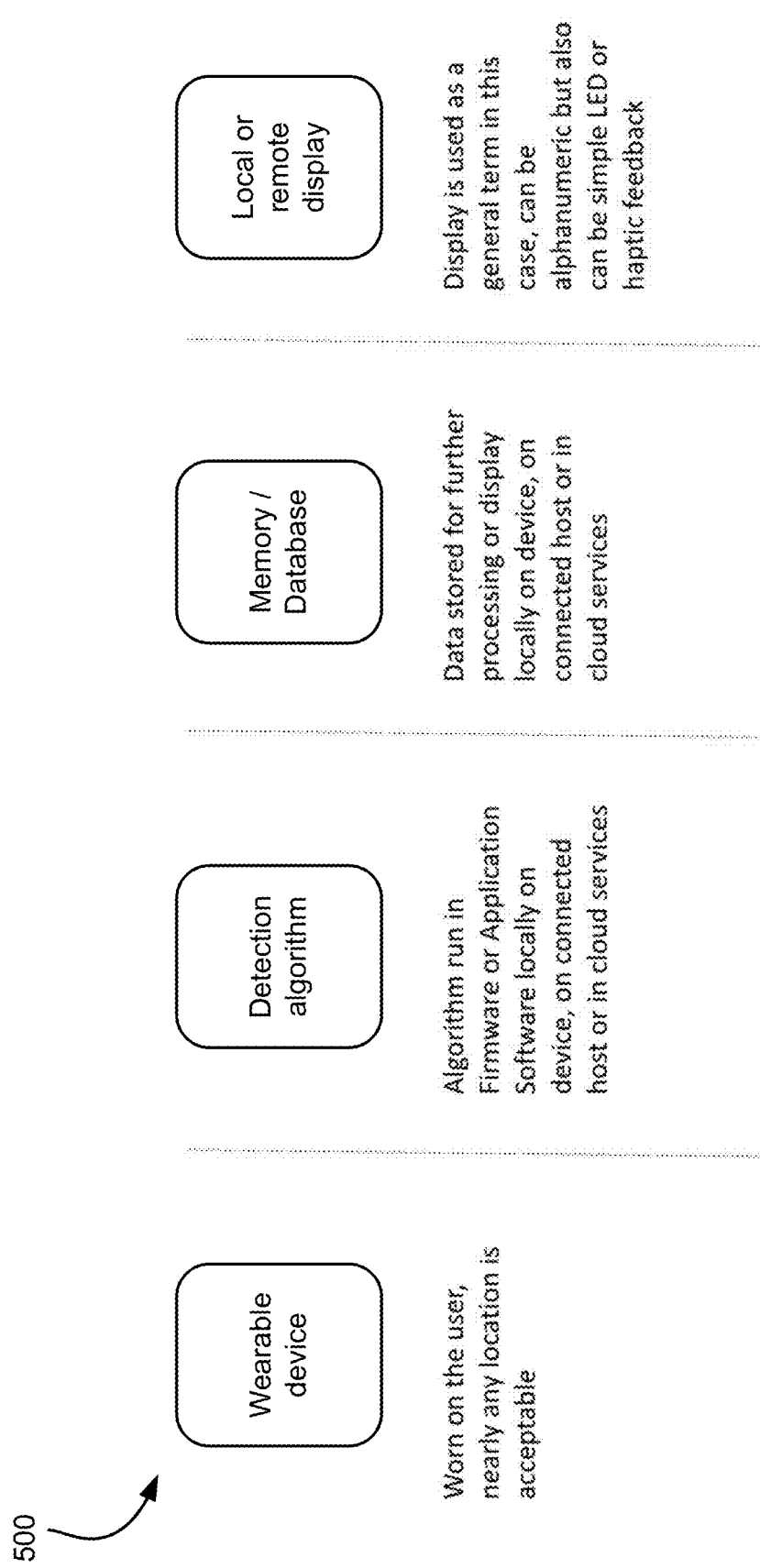
FIG. 5 is a graphical representation of an illustrative implementation utilized by the wearable device to detect resonance breathing.

FIG. 5 is a graphical representation 500 of an illustrative implementation utilized by the wearable device to detect resonance breathing. While each of these blocks are sequential in layout, the entirety of the operation may be a closed loop system whereby one or more of the included blocks may have feedback loops to the other blocks, adjusting appropriate parameters to change device detection and operational behavior to ensure that the data collected by the system is as accurate as possible, as well as shifting algorithm behavior to synthesize that which is deemed missing and/or inaccurate. Inaccuracies in data can be detected utilizing existing data, acted upon via algorithms as described in the previous paragraphs of this section, which are then referenced via additional algorithms which calculate, in parallel, an ideal data set that represents perfect resonance for that data. Based on this continuous comparison, parameters within the device that control the sensors and/or other algorithmic inputs may be adjusted to allow for the collection of better data for the specific user at the specific time in the specific environment.

Utilizing Multiple Sensor Systems in a Wearable Device to Modify Device Behavior A wearable device that may be positioned at a location on the user's body, for example wrist, ear, chest, neck or otherwise, can utilize multiple onboard sensors in or on a housing thereof, as well as sensors remotely connected, to modify the device's behavior for any reason, such as to optimize the user experience. Items that may be controlled include device power consumption to extend battery longevity, sensor sample rates to gather more or less data as well as other more complex matrices of system controls that extend to the way the device communicates with a remote host and/or reacts to user interface stimuli.

A multi-sensor wearable device such as any of those described herein may be configured to utilize its own sensor input data to control device behavior. Some elements from the devices' sensor arrays may be, but are not limited to, one or multiple (e.g., 3, 6, 9, etc.): axis accelerometers, optical and/or other non-visible light spectrum sensors such as IR receivers whether or not they are made up of an LED/receiver pair or if they are working in standalone fashion, thermal sensors, and/or internal power monitoring and feedback sensors.

Based upon the input from these sensors, the internal firmware, stored in a computer readable storage medium and running on a processing circuit of the wearable device, may enable modification of the wearable device behavior and place the wearable device into states that are not the current state. Examples of these state changes, also referred to herein as operational modes, may be to change the operating behavior of the wearable device from one operational mode such as actively sensing heartrate in a normal cadence manner to another operational mode which may increase the rate of sensor data acquisition from or by at least one of the sensors, such as by increasing the sampling rate of the sensor and/or the frequency of the cadence for heart rate waveform sensing. Other modes may include switching into an extremely low power storage mode, a beacon mode to allow the user to find a misplaced device, device sleeping mode to conserve device battery, a user sleep detection mode, etc. With each automated state change the wearable device may adjust internal algorithm parameters in one approach. Examples of algorithm parameters that may be algorithmically adjusted to adapt to certain observed conditions are the increase or decrease of various sensor sample rates to collect more or less accurate data as appropriate while increasing or decreasing power efficiency as a result.

In another approach, the automated state change of the wearable device may shift from a current subset of runtime operating code completely or entirely to an alternate subset of runtime operating code to perform the appropriate functions for that state.

Figure 6:
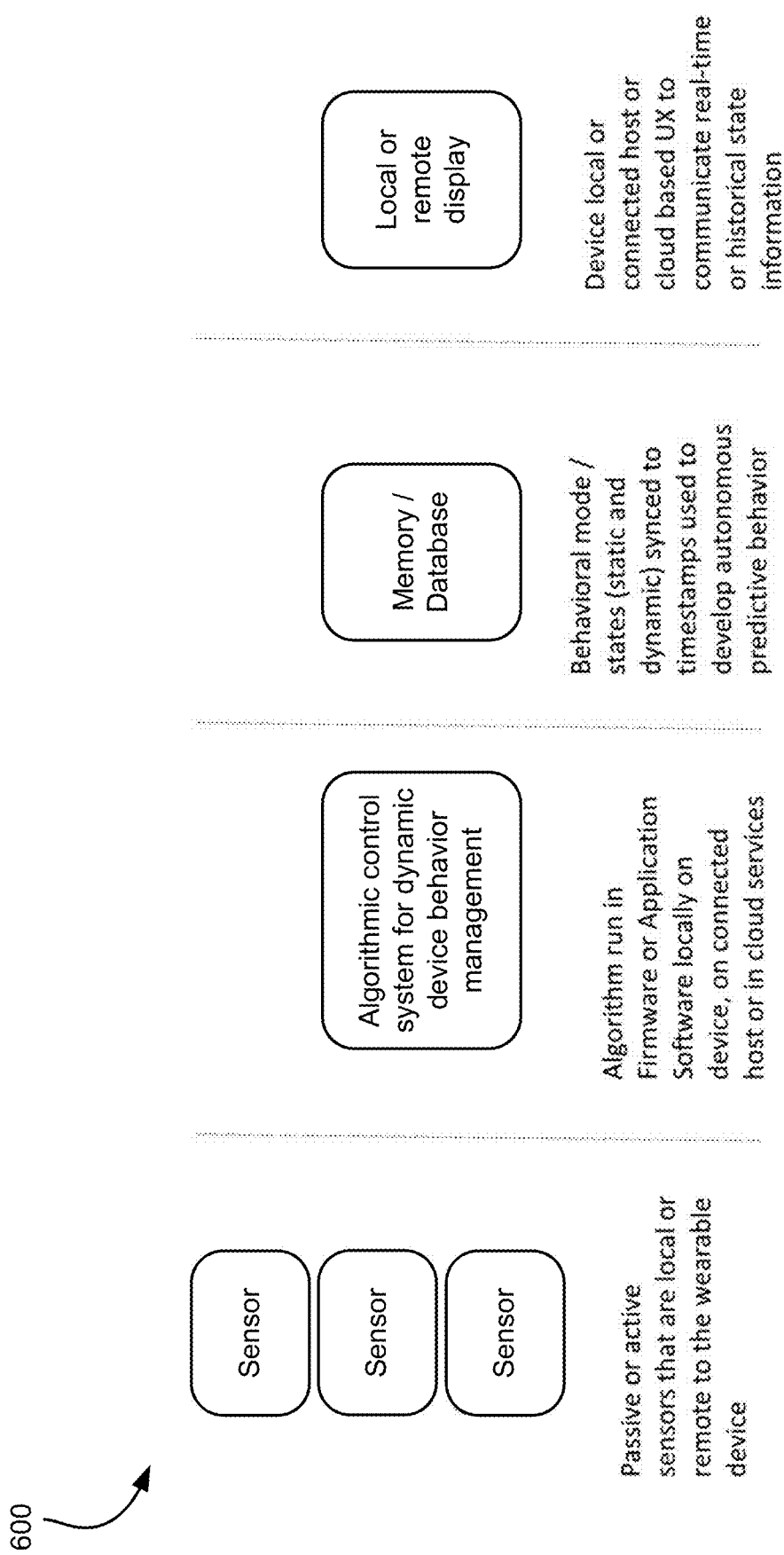
FIG. 6 is a graphical representation of a multi-sensor wearable device with the ability to concurrently process and act upon input data to change device behavior.

FIG. 6 is a graphical representation 600 of a multi-sensor wearable device with the ability to concurrently process and act upon input data to change device behavior. The sensors are can be multitasked with other primary functions of the wearable device such as heart rate waveform detection and/or step counting but they also may be included as a single function sensor with the only purpose being to detect parameters in and around the wearable device upon which the internal algorithms may act to change device behavior.

The algorithms included in the second block of FIG. 6 can be developed and stored in ROM and/or nonvolatile memory with tunable parameters that are received from the runtime operational code and/or connected application and/or cloud. These algorithms can also be stored dynamically in nonvolatile memory, e.g., Flash, as well with independent behaviors developed for specific users or subsets of users, such as when a user is on a pre-planned or logged type training plan which may include physical as well as mental stimuli and feedback for a team of users whose goals are set and monitored by an expert coach or mentor, with data from the sensors being used to modify behavior of the devices that each team member is using for the coach or mentor to review and receive only pertinent valuable data of their choice.

The local and/or remote display on the wearable device is able to provide immediate and/or delayed feedback to the user and to others regarding the state of the wearable device. When the wearable device's mode has been changed due to sensor input data acted upon by the device's algorithms, a local and/or remote output device can be enabled to notify the user of the change of state. These outputs/output devices can include items such as a pulsed vibration, an LED and/or other simplified visual indication utilizing color, an OLED display on the device and/or a change in state on a remote monitoring panel which can vary from as simple as an audible notification and/or single LED color change, to as complex a full display on a computer screen showing the from and to states along with the driving sensor input items that initiated the change.

Utilizing Machine Learning Algorithms to Analyze Historical and Real-Time Data to Predictively Control Operational States on a Wearable Device Wearable devices that may be positioned at some location on the user's body, for example wrist, ear, chest, neck or otherwise, can utilize multiple onboard sensors, as well as any sensors remotely connected thereto, to collect data that can be stored and/or processed in real time using machine learning algorithms (MLAs) to predictively control the behavior of one or more wearable devices. Data so stored may be considered historical sensor data. The dynamic algorithms may use incoming time stamped data to establish complex behavioral patterns and mode switch activities on those wearable devices to match upcoming expected events. Should an expected event fail to occur, the sensor data may reflect this new information and the MLA may adjust accordingly.

Wearable devices with single or multiple sensors collect data which may be both immediately actionable as well as historically relevant. The immediately actionable data from the wearable devices such as steps, heart rate, heart rate R-R Interval, temperature, blood pressure, VO2 max, location and/or other information has an even greater value when it is post processed relative to time as well as all of the other data combined. VO2 max is the measurement of the maximum amount of oxygen that an individual can utilize during a specified period, usually during intense, or maximal exercise. It is measured as milliliters of oxygen used in one minute per kilogram of body weight. VO2 max is also referred to in the art as maximal oxygen consumption, maximal oxygen uptake, and max VO2.

An example of how a machine learning algorithm can be implemented to provide a use case for stored multiple sensor data, according to one embodiment, is for a user's data to be stored on the wearable device, in the connected host and/or in the cloud, where it is then operated upon to predict the next device state and provide the user with a prompt to engage in a regularly scheduled event. The event or series of events leading up to the desired behavior may be that a user brushes their teeth in the morning followed by the drinking of coffee as part of their morning routine. The user may have then engaged in a paced breathing meditation session utilizing a companion application for a series of days leading up to the current date and time. The device itself may then provide a pre-emptive prompt to the user's wearable device and/or to the user's companion device to ask the user if he or she wants to continue the previous activity pattern and/or if he or she would like to provide even further input to the system, such as whether this input is only valid as a pattern on weekdays or weekends.

Other such post-processed data analysis leading to predictive behavior and/or input for a user may include the analysis of biometric data such as heart rate, its waveform and/or stress information associated with certain times, locations, activities, people, places and/or other things and events, which may allow a companion application to output an alert (via the host or wearable device) to the user of the upcoming situation and/or condition and allow the user to utilize built-in coping exercises installed on the wearable itself, shown on the connected companion host device and/or via a cloud based server delivery system.

Figure 7:
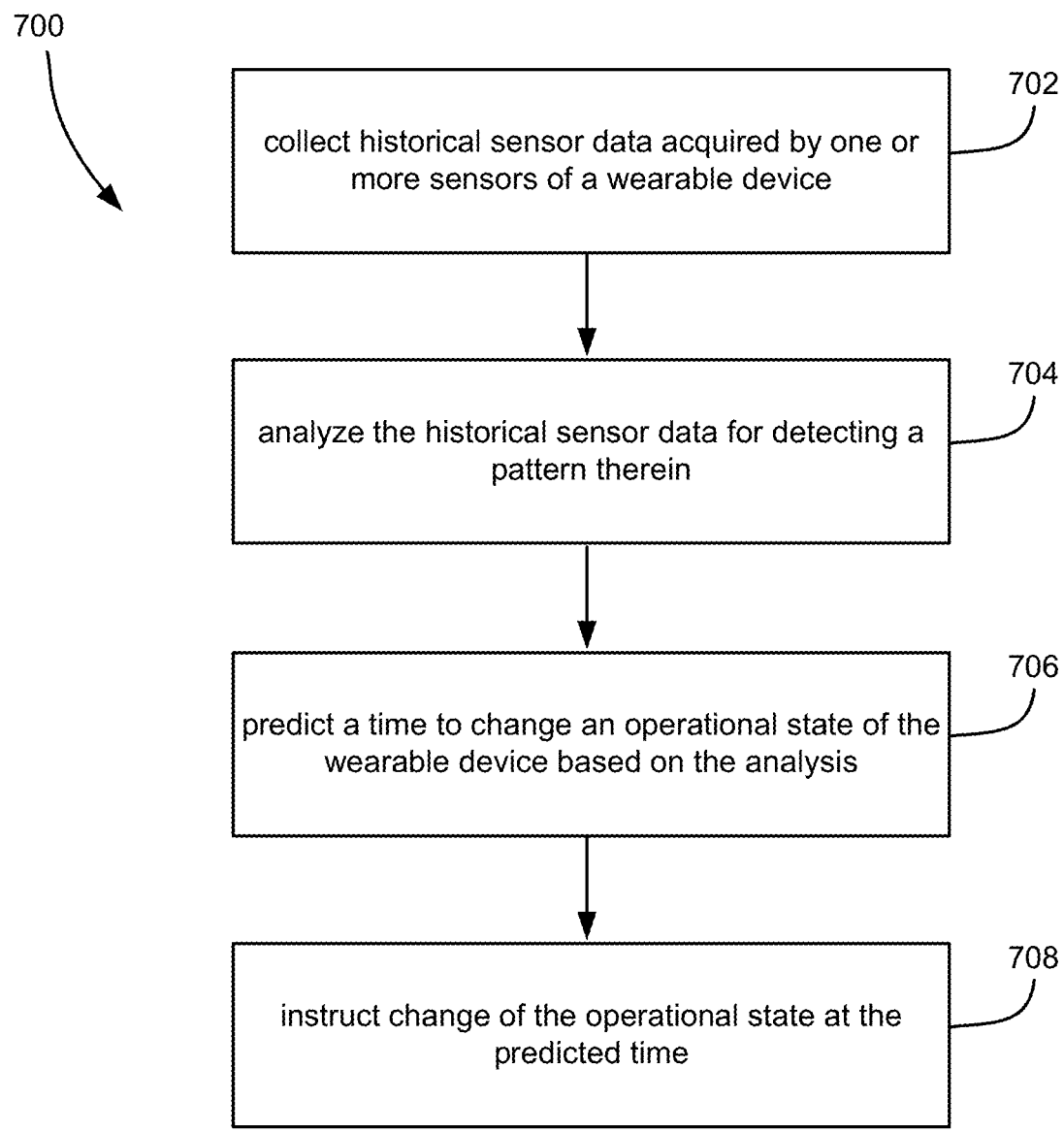
FIG. 7 is a flowchart of a method for predictively controlling an operational state of a wearable device, in accordance with one embodiment.

FIG. 7 shows a method 700 for predictively controlling an operational state of a wearable device, in accordance with one embodiment. As an option, the present method 700 may be implemented in conjunction with wearable devices such as those shown in the other FIGS. described herein, on a host, on a remote server, etc. Further, the methods presented herein may be carried out in any desired environment. Moreover, more or less operations than those shown in FIG. 7 may be included in method 700, according to various embodiments. It should also be noted that any of the aforementioned features may be used in any of the embodiments described in accordance with the various methods.

In operation 702, historical sensor data acquired by one or more sensors of a wearable device is collected. In operation 704, the historical sensor data may be analyzed for detecting a pattern therein. In operation 706, a time to change an operational state of the wearable device is predicted based on the analysis. In operation 708, change of the operational state at the predicted time is instructed. A change in operational state may be any change in operation of the wearable device.

Figure 8:
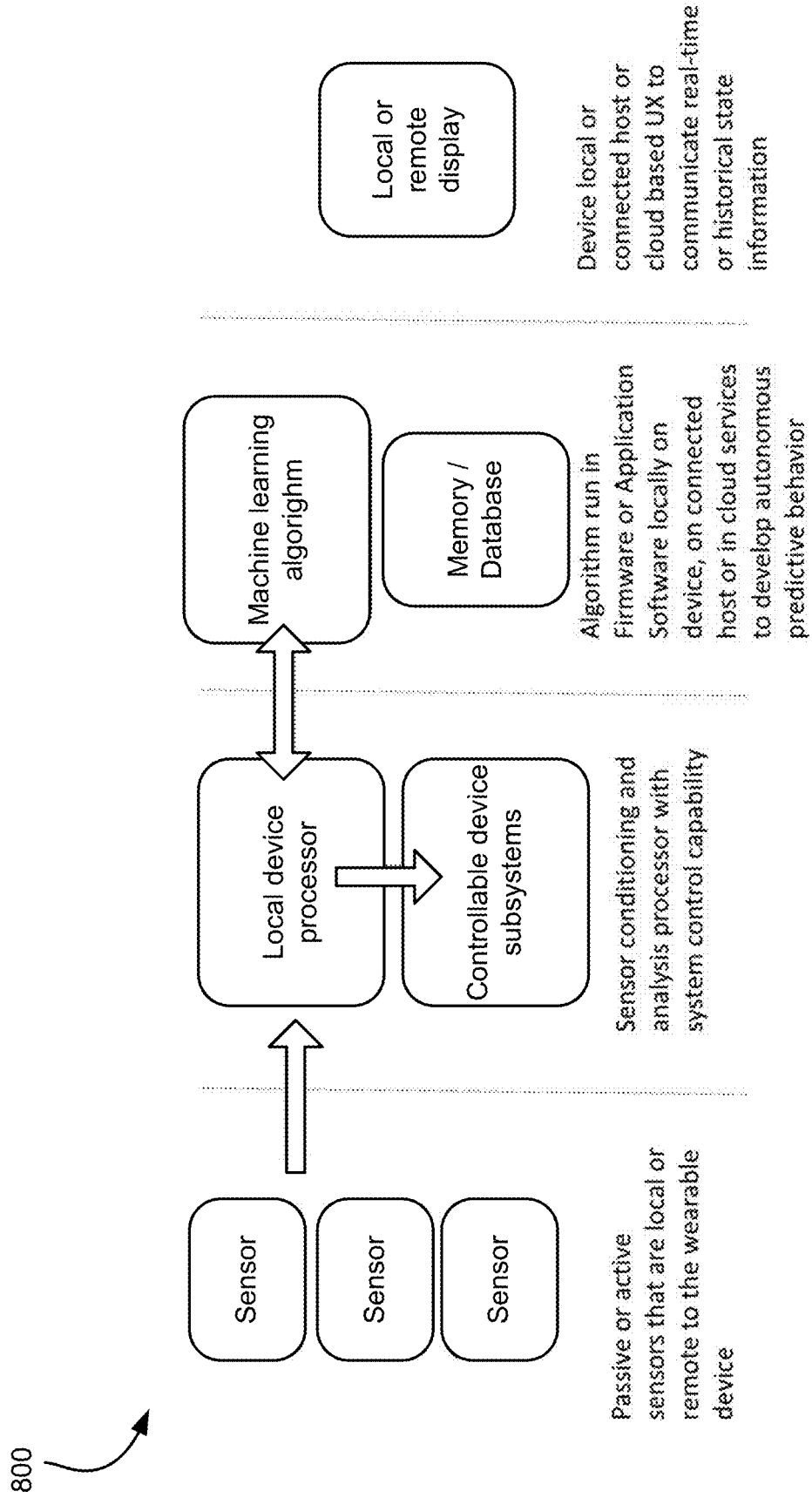
FIG. 8 is a graphical representation of a multi-sensor wearable device system with an onboard processor that utilizes the data received from the sensors to modify parameters on locally controllable algorithms.

FIG. 8 is a graphical representation 800 of a multi-sensor wearable device system with an onboard processor that utilizes the data received from the sensors to modify parameters on locally controllable algorithms. This system also includes a block that represents a machine learning system that can be located locally to the wearable device and/or on a connected host device such as a smartphone, tablet, etc. which can then be connected to a tertiary remote display system and/or cloud processing architecture for remote data analysis and algorithm design.

Filtering Raw Heart Rate Signal Data Based Upon Multi-Sensor Contextual Environmental Information A wearable device that may be positioned at some location on the user's body, for example wrist, ear, chest, neck or otherwise, can utilize multiple onboard sensors to collect high resolution heart rate signal data (beats per minute (BPM), R-R interval (RRi), Heart Rate Variability (HRV) metrics, etc.) as well as other relevant informative factors that, when used in conjunction as a complex system, can be utilized to present the user with accurate and valuable heart rate metrics such as a Daily Heart Rate Variability (Daily HRV) score (and/or other outputs) upon which decisions can be made by the user to take further beneficial actions.

If statistical analysis is performed on heart rate signal data without significant contextual information gathered both from the direct heart rate signal as well as the environment surrounding the collected heart rate signal, the resulting values may be erroneous. Multi-variable filtering may be used to condition data before an accurate value can be obtained.

Algorithms may operate on the wearable device and/or in the connected host to analyze all sensor data that is collected in a simultaneous fashion to allow advanced filtering to occur on that data, which in turn results in a more accurate subset of real data upon which downstream algorithms can process. For example, various environmental and user conditions can lead to erroneous data collection and therefore it is advantageous to utilize sensors that measure those conditions to act as input to filtering algorithms to remove error. Conditions can vary from static items such as user skin tone to dynamic environmental conditions such as ambient temperature, skin surface moisture content or even the ambient light of the user with blockers such as periodic flicker due to sinusoidal power supplies (50 Hz or 60 Hz) or randomized light from outdoor exposure to a range of constantly changing sunlight conditions such as full sunlight to shade to night.

Figure 9:
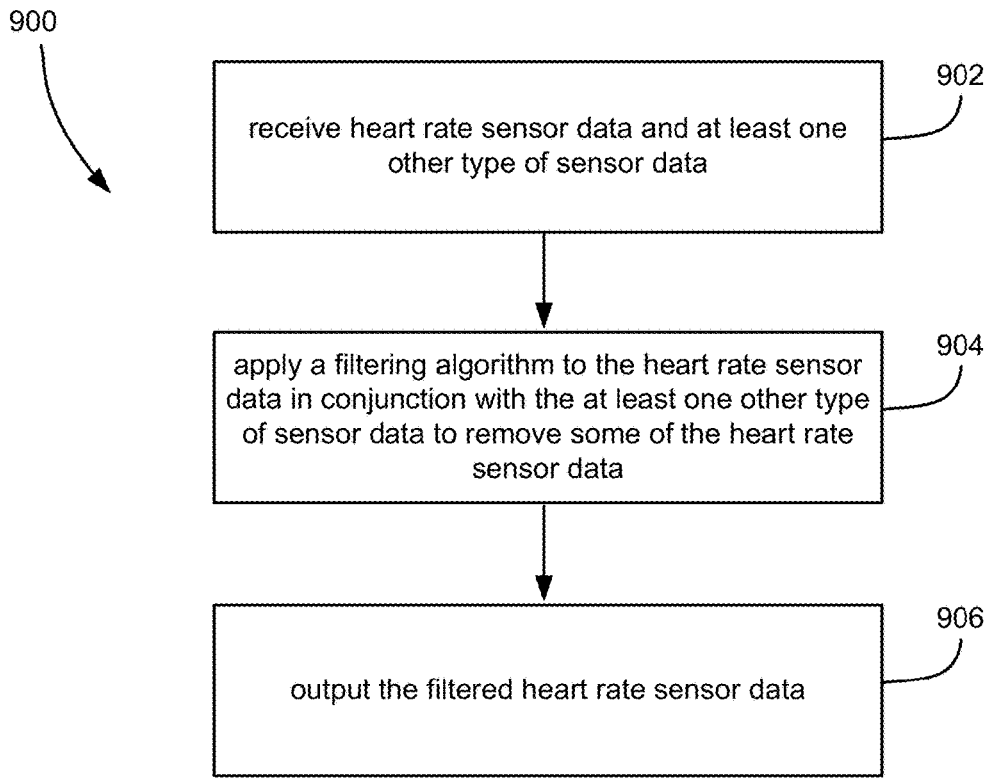
FIG. 9 is a flowchart of a method for filtering heart rate signal sensor data based upon multi-sensor contextual environmental information, in accordance with one embodiment.

FIG. 9 shows a method 900 for filtering heart rate signal sensor data based upon multi-sensor contextual environmental information, in accordance with one embodiment. As an option, the present method 900 may be implemented in environments such as those shown in the other FIGS. described herein. Further, the methods presented herein may be carried out in any desired environment. Moreover, more or less operations than those shown in FIG. 9 may be included in method 900, according to various embodiments. It should also be noted that any of the aforementioned features may be used in any of the embodiments described in accordance with the various methods.

In operation 902, heart rate signal sensor data, and at least one other type of sensor data, is received. A filtering algorithm is applied to the heart rate signal sensor data in conjunction with the at least one other type of sensor data to remove some of the heart rate signal sensor data. See operation 904. The filtered heart rate signal sensor data is output in operation 906.

Figure 10:
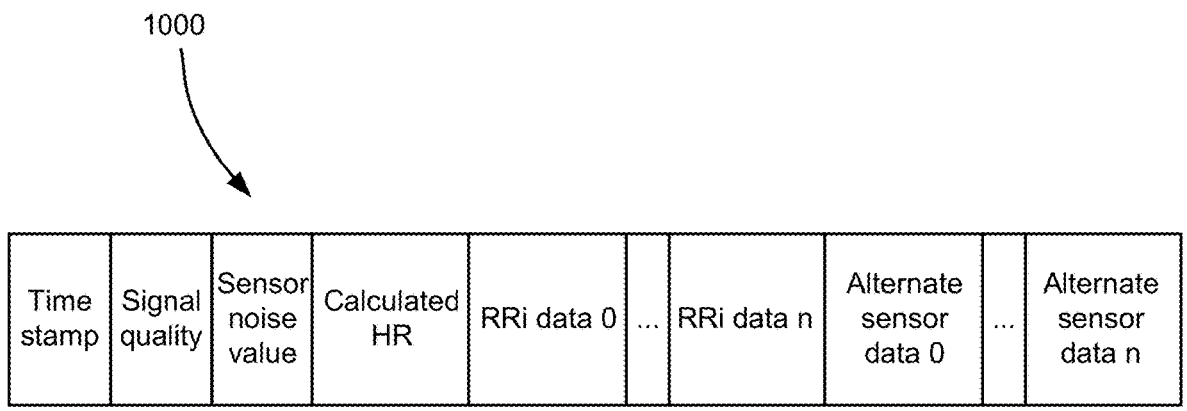
FIG. 10 graphically depicts a heart rate signal data structure with multi-variable input.

FIG. 10 graphically depicts a heart rate signal data structure 1000 with multi-variable input. Various data elements in the structure 1000 include the following:
Time stamp
Signal quality
Sensor noise value
Calculated heart rate (HR)
RRi data 0 . . . n
Alternate sensor data 0 . . . n.

As shown in FIG. 10, a multi-sensor equipped wearable device may gather not only the data of interest for calculating heart rate in BPM format but may also collect data from other types of sensors such as those described in the Sensor System section above. A data collection and packing system may operate on all of this data, time stamped so as to be aligned within the collection time domain. The data collected in this manner can be stored directly into the memory subsystems, Flash and/or RAM on the wearable device, various memory structures such as Flash on the host device and/or in a cloud based storage system such as Amazon Web Services. The data can also be compressed and/or compartmentalized using various lossless compression techniques to reduce overall storage capacity requirements without losing actionable data.

Algorithms being performed on the wearable device, host and/or cloud server can then act upon this data in real time and/or at a future date and provide the user with highly accurate information regarding their biometric state including heart rate, R-R interval, VO2 Max, Caloric expenditure, etc.

Figure 11A:
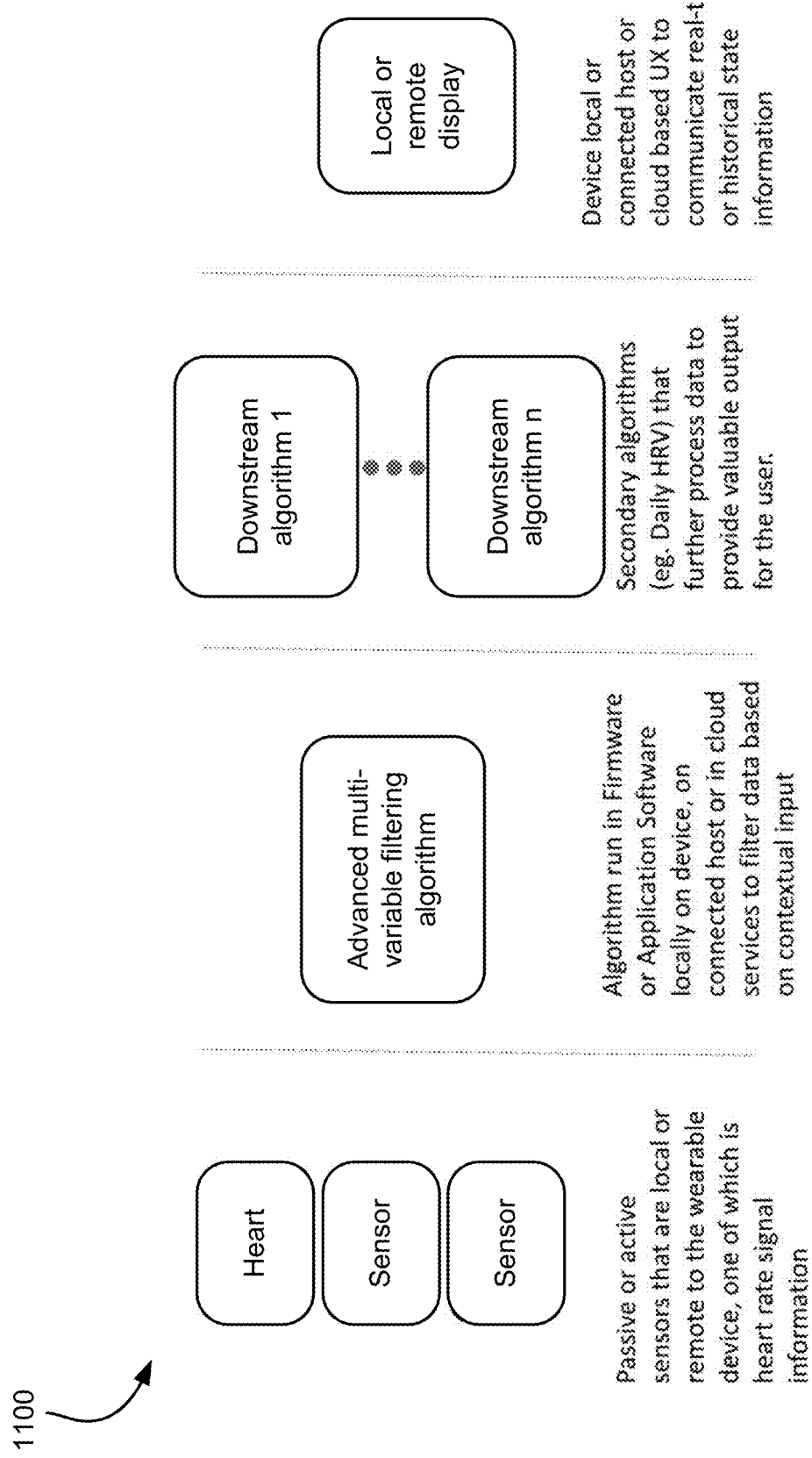
FIG. 11A is a graphical representation depicting a system which takes input from a multi-sensor array, pre-processes the data from the array and then passes the filtered, valid output data to downstream algorithms.

FIG. 11A is a graphical representation 1100 depicting a methodology used by this specific system to take input from a multi-sensor array, pre-process the data from the array and then pass the filtered, valid output data to the downstream algorithms which need not have awareness of the filtering mechanism to operate properly.

Functions that the filtering algorithm can account for include the ability to remove, e.g., window out, data that is not pertinent to downstream algorithms. This filtering, for example, may remove extraneous system noise resulting from the user placing the device incorrectly on the body location specified for collection of data. Other filtering may remove data that is specifically invalid for the downstream algorithms such as data collected when the user's heart rate is higher than a specified value, which would create data that is not relevant for Heart Rate Variability (HRV) data analysis.

An Operational Method to Calculate an Accurate Representation of Energy Expenditure Across all Ranges of Activity from Sedentary Through Extreme Activity Utilizing a Body Worn Wearable Device A wearable device that may be positioned at some location on the user's body, for example wrist, ear, chest, neck or otherwise, can utilize multiple onboard sensors to collect information on the user (such as heart rate signal information, motion, temperature, etc.) which can then be translated into values for energy expenditure (calories). While prior techniques were only valid within limited ranges, various approaches described herein are accurate across a wide range of user activity levels, and in some cases, across all user activity levels.

Utilizing an advanced algorithm run on the wearable device, on a connected host's processor and/or in a connected cloud based processing architecture, an accurate representation of overall energy expenditure can be produced. For example, the filtered heart rate signal sensor data described in the previous section may be used in various algorithms presented in this section.

Figure 11B:
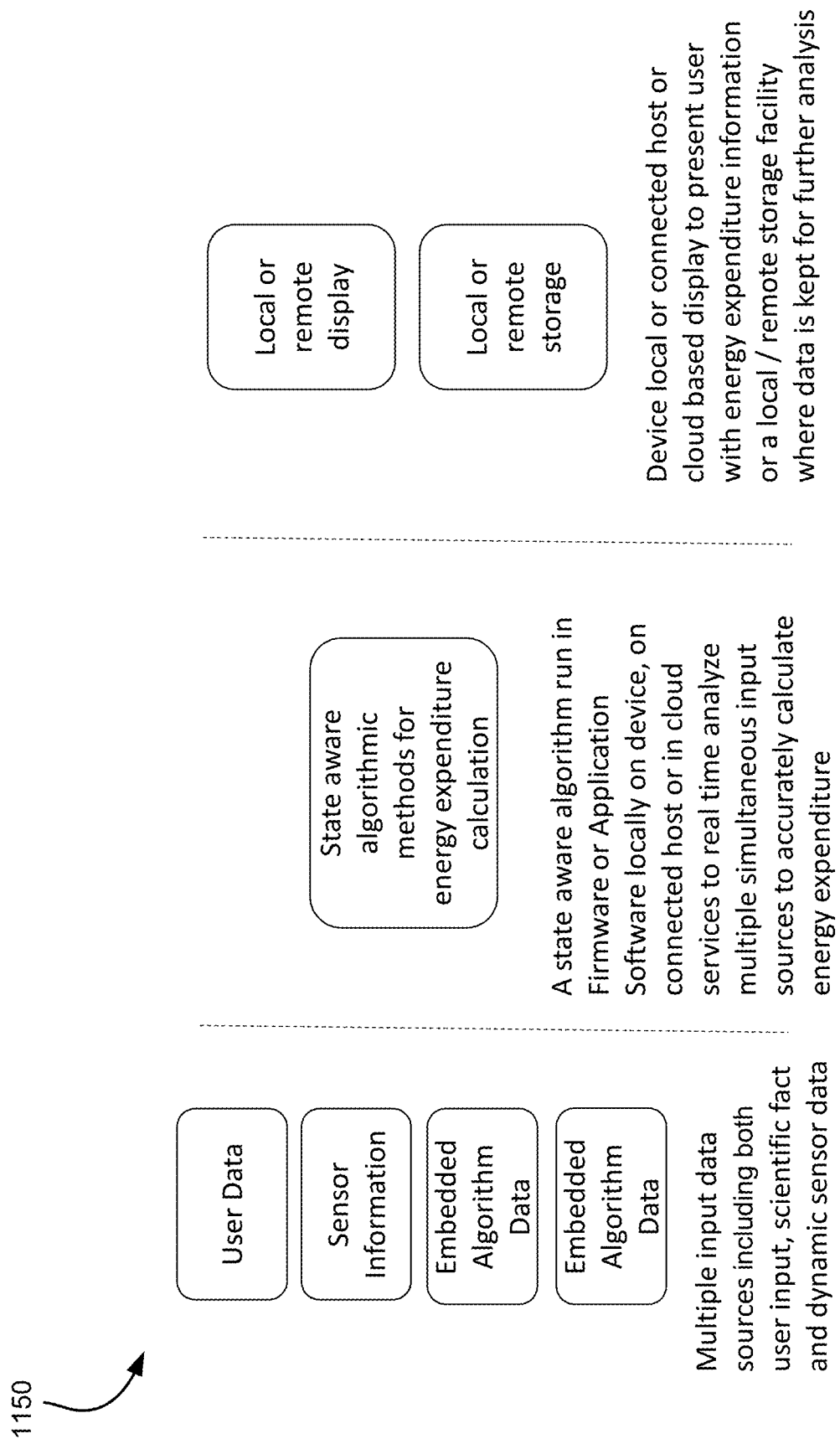
FIG. 11B is a graphical representation depicting a system for accurately determining energy expenditure from multiple input variables.

FIG. 11B is a graphical representation 1150 of a system that integrates multiple input sources and algorithms/mathematical equations to perform state-aware algorithmic methods for accurately determining energy expenditure from multiple input variables. Illustrative input sources include user data of any type, sensor data, and/or embedded algorithm data. Known equations/algorithms, and/or equations and algorithms presented elsewhere herein can be used to accurately determine energy expenditure from the input variables.

Prior to the present disclosure, attempts to use a multi-sensor wearable device to calculate energy expenditure were conducted, most often with significant error, due to various calculation methods such as developed by Wicks and/or Keytel and/or Modified Keytel alone. These energy expenditure equations have limitations based on the amount of activity the user is currently partaking in as well as the gender of the user which, if both conditions are not specified or accounted for correctly, e.g., the user's body and therefore heartrate is not operating within the appropriate HR zone, then the values can be off upwards of 20%-30%.

Known methodologies such those from Wicks et al. to more easily calculate (measure) METs utilizing HR measurement may be implemented in various embodiments presented herein. A text abstract from PubMed that explains the methods used by Wicks et al. is available at https://www.ncbi.nlm.nih.gov/pubmed/21364476.

Energy expenditure measured in METs is widely used in cardiovascular medicine, exercise physiology, and nutrition assessment. However, measurement of METs requires complex equipment to determine oxygen uptake. A simple method to predict oxygen uptake on the basis of HR measurements without requirement for gas analysis, movement-recording devices, or exercise equipment (treadmills, cycle ergometers) would enable a simple prediction of energy expenditure. Various embodiments use HR to accurately predict oxygen uptake.

Published studies that reported a measured resting HR (HR(rest)), a measured activity HR (HR(absolute)), and a measured oxygen uptake (mL O(2)·kg(−1)·min(−1)) associated with the HR(absolute) were identified. A total of 220 data sets were extracted from 60 published exercise studies (total subject cohort=11,257) involving a diverse range of age, pathophysiology, and the presence/absence of β-blocker therapy. Net HR (HR(net)=HR(absolute)−HR (rest)) and HR index (HR(index)=HR(absolute)/HR(rest)) were calculated from the HR data. A regression analysis of oxygen uptake (expressed as METs) was performed against HR(absolute), HR(net), and HR(index).

Statistical models for the relationship between METs and the different HR parameters (HR(absolute), HR(net), and HR(index)) have been developed. A comparison between regression analyses for the models and the actual data extracted from the published studies demonstrated that the best fit model was the regression equation describing the relationship between HR(index) and METs. Subgroup analyses of clinical state (normal, pathology), testing device (cycle ergometer, treadmill), test protocol (maximal, submaximal), gender, and the effect of β-blockade were all consistent with combined data analysis, demonstrating the robustness of the equation.

Various approaches may use HR(index) to predict energy expenditure with the equation METs=6HR(index)−5.

Also, below is an abstract and equations developed by L R Keytel, J H Goedecke, T D Noakes, H Hiiloskorpi, R Laukkanan, L van der Merwe and E V Lambert in their study titled "Prediction of energy expenditure from heart rate monitoring during submaximal exercise." As referenced to PubMed (https://www.ncbi.nlm.nih.gov/pubmed/15966347) as well as Shapesense's online caloric calculator (http://www.shapesense.com/fitness-exercise/calculators/heart-rate-based-calorie-burn-calculator.shtml). Techniques, information and equations described therein and below may be used to calculate energy expenditure in various approaches.

[Abstract:] The aims of this study were to quantify the effects of factors such as mode of exercise, body composition and training on the relationship between heart rate and physical activity energy expenditure (measured in kJ×min(−1)) and to develop prediction equations for energy expenditure from heart rate. Regularly exercising individuals (n=115; age 18-45 years, body mass 47-120 kg) underwent a test for maximal oxygen uptake (VO2max test), using incremental protocols on either a cycle ergometer or treadmill; VO2max ranged from 27 to 81 ml×kg(−1)×min(−1). The participants then completed three steady-state exercise stages on either the treadmill (10 min) or the cycle ergometer (15 min) at 35%, 62% and 80% of VO2max, corresponding to 57%, 77% and 90% of maximal heart rate. Heart rate and respiratory exchange ratio data were collected during each stage. A mixed-model analysis identified gender, heart rate, weight, V2max and age as factors that best predicted the relationship between heart rate and energy expenditure. The model (with the highest likelihood ratio) was used to estimate energy expenditure. The correlation coefficient (r) between the measured and estimated energy expenditure was 0.913. The model therefore accounted for 83.3% (R2) of the variance in energy expenditure in this sample. Because a measure of fitness, such as VO2max, is not always available, a model without VO2max included was also fitted. The correlation coefficient between the measured energy expenditure and estimates from the mixed model without VO2max was 0.857. It follows that the model without a fitness measure accounted for 73.4% of the variance in energy expenditure in this sample. Based on these results, we conclude that it is possible to estimate physical activity energy expenditure from heart rate in a group of individuals with a great deal of accuracy, after adjusting for age, gender, body mass and fitness.

Formulas for Determination of Calorie Burn if VO2max is Unknown $$\text{Male: } ((-55.0969+(0.6309\times HR)+(0.1988\times W)+ (0.2017\times A))/4.184)\times 60\times T$$

$$\text{Female: } ((-20.4022+(0.4472\times HR)-(0.1263\times W)+ (0.074\times A))/4.184)\times 60\times T$$

where
HR=Heart rate (in beats/minute)
W=Weight (in kilograms)
A=Age (in years)
T=Exercise duration time (in hours)

Formulas for Determination of Calorie Burn if VO2max is Known $$\text{Male: } ((-95.7735+(0.634\times HR)+(0.404\times VO2\text{max})+ (0.394\times W)+(0.271\times A))/4.184)\times 60\times T$$

$$\text{Female: } ((-59.3954+(0.45\times HR)+(0.380\times VO2\text{max})+ (0.103\times W)+(0.274\times A))/4.184)\times 60\times T$$

where
HR=Heart rate (in beats/minute)
VO2max=Maximal oxygen consumption (in mL·kg−1·min−1)
W=Weight (in kilograms)
A=Age (in years)
T=Exercise duration time (in hours)

Formula for Determination of Maximum Heart Rate Based on Age $$\text{Maximum Heart Rate (beats/minute)}=208\times(0.7\times\text{Age})$$

Formula for Exercise Intensity Conversion from % MHR to % VO2max $$\%\ VO2\text{max}=1.5472\times\%\ MHR-57.53$$

where
% MHR=Percentage of maximum heart rate
% VO2max=Percentage of VO2max

In one approach, the algorithm utilizes multiple sensors as input to a combination of these calorie burn calculations as well as lookup tables to fit dynamic algorithm parameter data into the algorithms prior to calculating a resultant caloric expenditure achieving a more accurate result. Lookup table data may include, but is not limited to basal caloric expenditure values, maximum HR calculations, age- and gender-specific values, floor and ceiling filtering parameters to tune and shift algorithms based on state aware sensors and variables, etc.

Utilizing Real-Time Feedback to Guide Advanced Breathing Meditation Techniques Incorporated Into a System That Can Operate in a Standalone Environment or Within a Connected Host/Device Relationship A wearable device that may be positioned at some location on the user's body, for example wrist, ear, chest, neck or otherwise, can utilize multiple onboard sensors to collect information on the user (such as heart rate, motion, temperature, etc.) which can then be used by onboard and/or external processing devices to create a closed loop system of guidance whereby the devices work in conjunction to deliver a feedback based paced breathing meditation experience.

A system configured such that cardiography such as BPM, RRi and/or HRV metrics, can be collected, filtered and acted upon in real time such that a user can be trained to incorporate feedback via visual, mechanical and/or audible stimuli and/or a combination of these feedback methods to change the user's breathing pace which in turn allows identification of each user's own specific resonant frequency.

Figure 12:
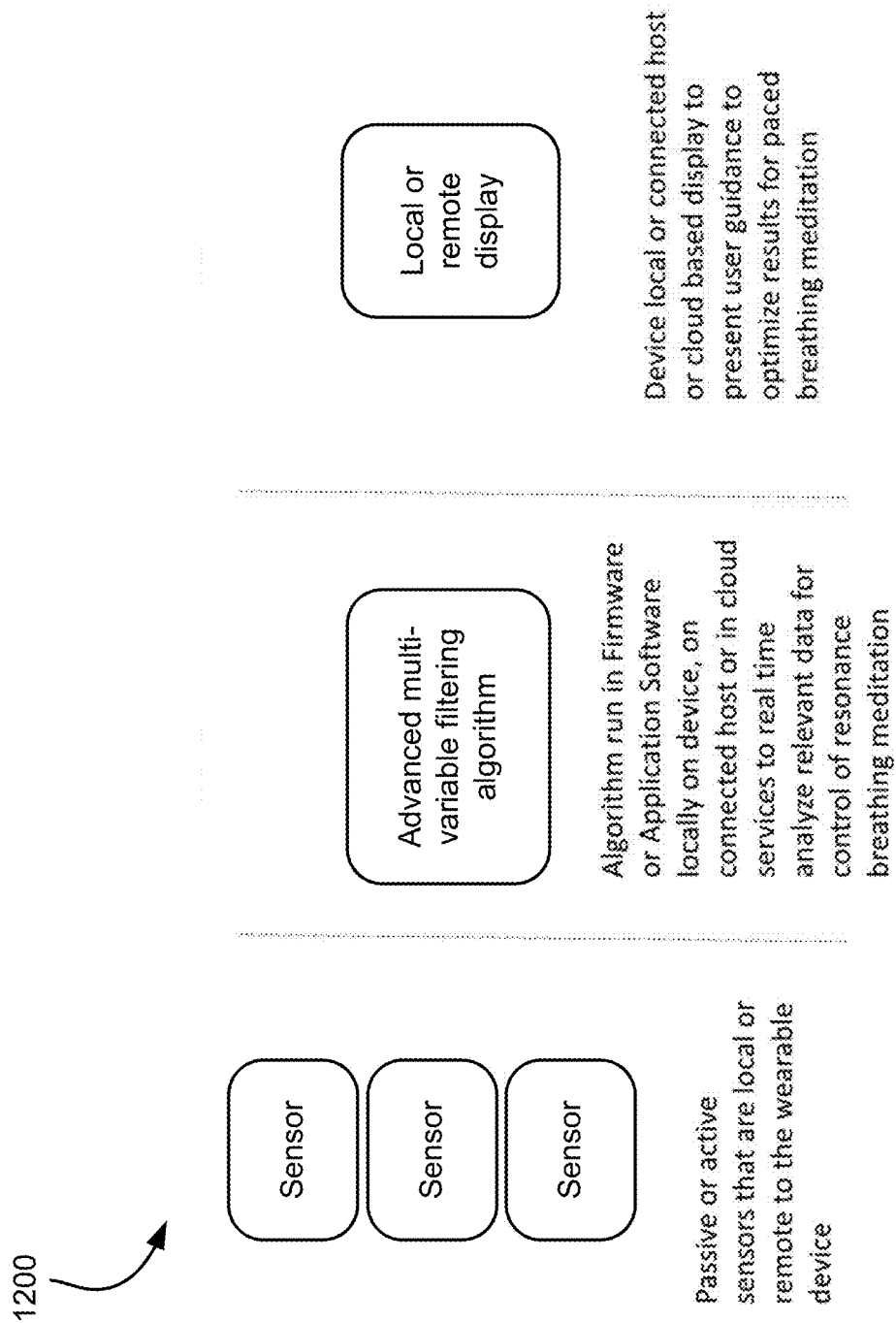
FIG. 12 is a graphical representation of a multi-sensor wearable device that includes the ability to filter data from one or more of its sensors.

FIG. 12 is a graphical representation 1200 of a multi-sensor wearable device that includes the ability to filter data from one or more of its sensors to then modify the feedback on the device locally, on a remotely connected host and/or a cloud based processor system with a visual and/or audible display.

Figure 13:
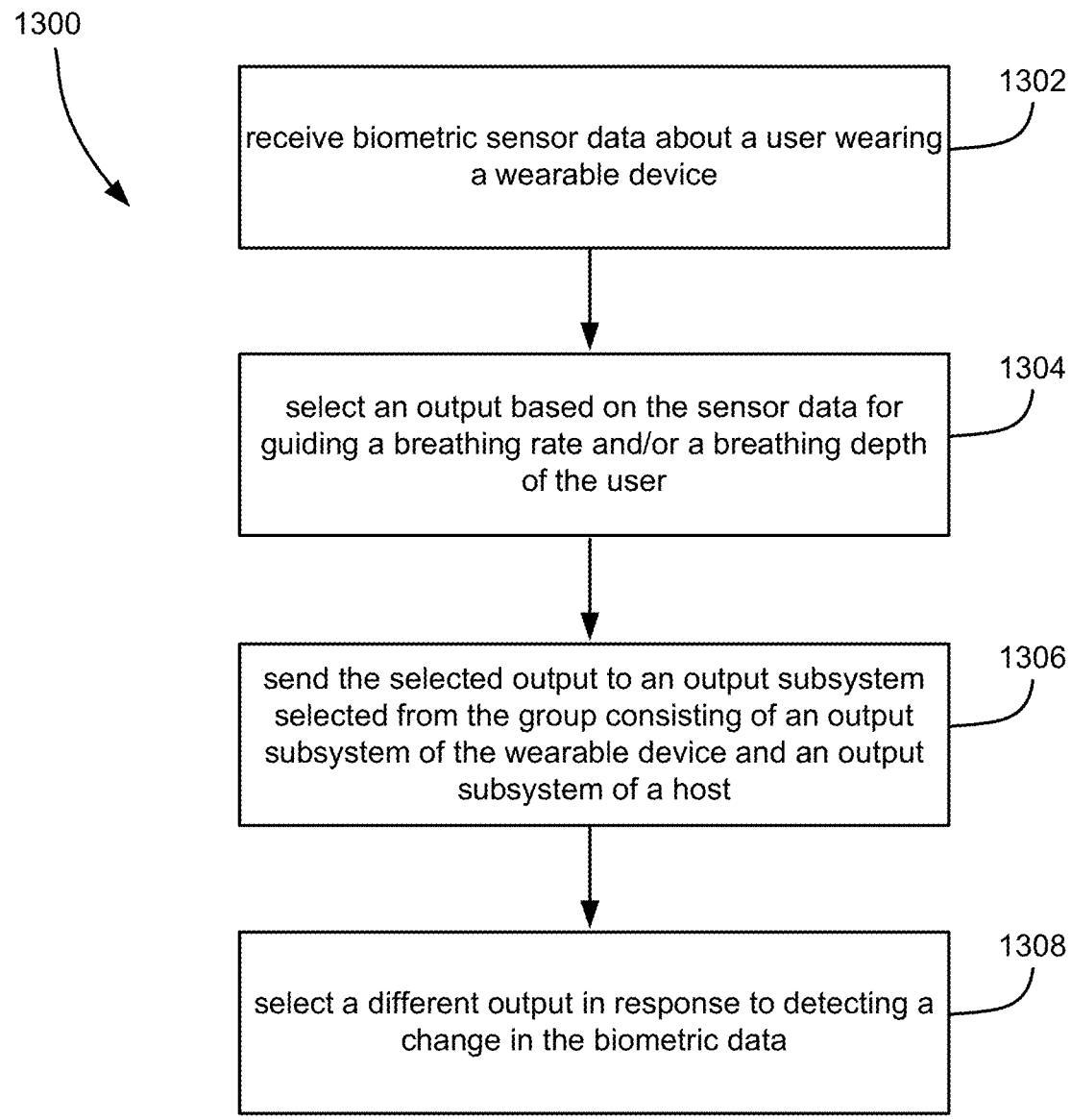
FIG. 13 is a flowchart of a method for utilizing real-time sensor data to guide breathing, in accordance with one embodiment.

FIG. 13 shows a method 1300 for utilizing real-time sensor data to guide breathing, in accordance with one embodiment. As an option, the present method 1300 may be implemented with devices such as those shown in the other FIGS. described herein. Further, the methods presented herein may be carried out in any desired environment. Moreover, more or less operations than those shown in FIG. 13 may be included in method 1300, according to various embodiments. It should also be noted that any of the aforementioned features may be used in any of the embodiments described in accordance with the various methods.

In operation 1302, biometric sensor data about a user wearing a wearable device is received. In operation 1304, an output is selected based on the sensor data for guiding a breathing rate and/or a breathing depth of the user. In operation 1306, the selected output is sent to an output subsystem selected from the group consisting of an output subsystem of the wearable device and an output subsystem of a host. The biometric sensor data is monitored, and a different output is selected in response to detecting a change in the biometric data. See operation 1308.

Figure 14:
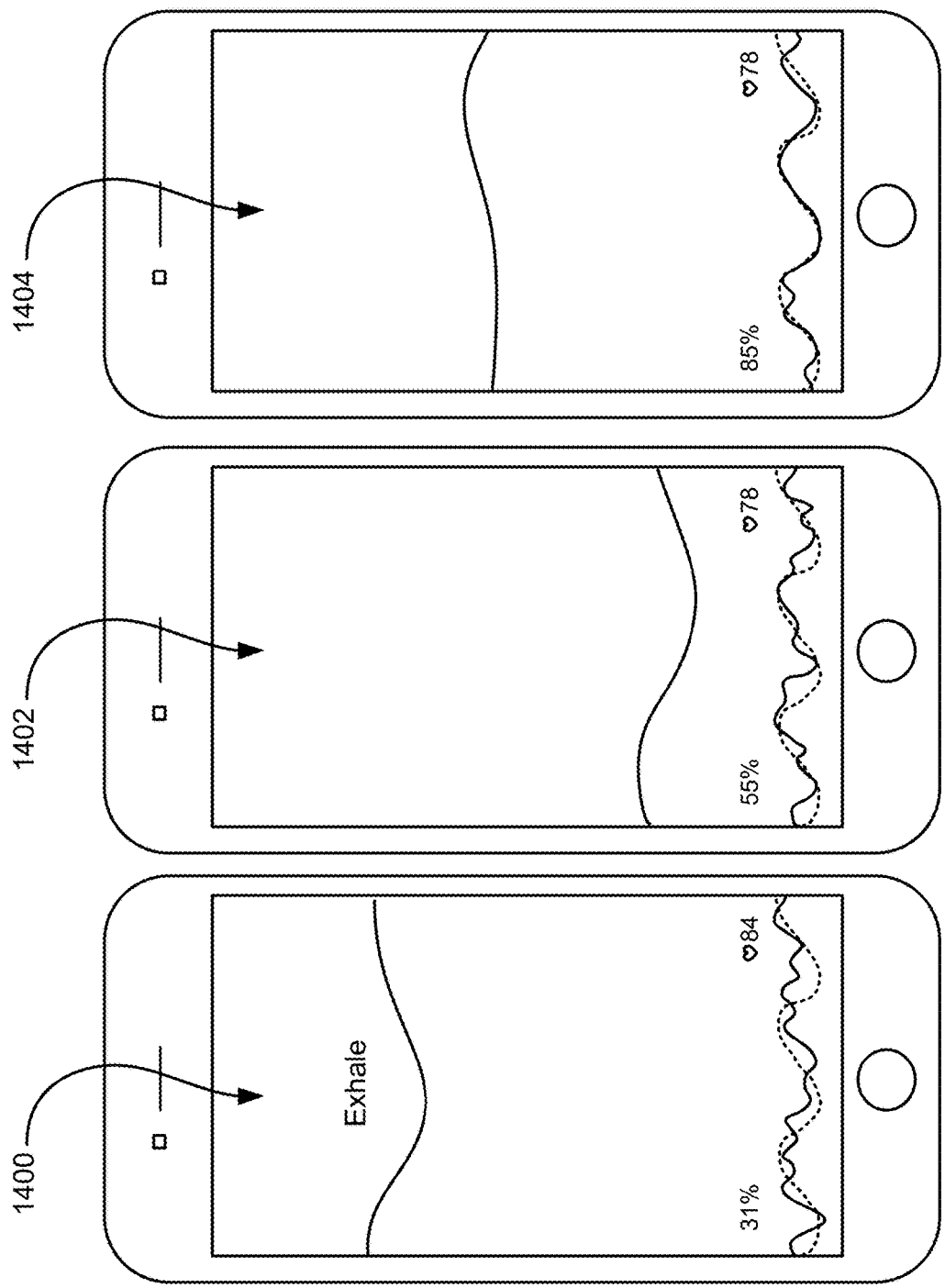
FIG. 14 is a depiction of several graphical display outputs that can be presented to the user when performing a paced breathing meditation session.

FIG. 14 shows several graphical display outputs 1400, 1402, 1404 that can be presented to the user when performing a paced breathing meditation session with real-time audio, visual, or audio-visual feedback. After detecting and/or receiving confirmation that the user has correctly placed the wearable device on their body, the data collection system on the wearable device then synchronizes with the user's remote host device and/or a cloud based device to present visual stimuli. The stimuli may be dynamic in shape, size, contrast and/or other parameters, each of which are directly affected by the data collected by the wearable device. The device then guides the user, in this specific example, to breathe in at a modified rate and/or depth until the user reaches the level of desired resonance specified per the resonant breathing exercise. The entire experience preferably implements real-time data collection, data filtering and processing as well as graphical, audible and/or haptic sensation generation by the wearable device, connected host and/or cloud based storage and processing device.

Referring to output 1400, "31% is the current focus %. "84" is the current heart rate. The upper wavy line represents breathing. The dashed line at the bottom is the goal and remains static. The solid line at the bottom is animated, and is less aligned with the dashed goal line when the focus is low, and becomes more aligned as the focus increases, see e.g., the progression from output 1400 to 1402 to 1404. At 100% focus, the two lower lines would be perfectly aligned.

In one illustrative example, RRi data is collected from the wearable device, e.g., in real-time to an app running on a host. The RRi data is used to calculate a focus score, which we then display via these metrics at the bottom of the screen. The main metric is the focus score, which is then also shown via visual representation in how closely the user's signal conforms to the goal (e.g., 0% focus has the signal all over the place, 100% focus is a perfect sine wave matching the goal). This is used to provide feedback to the user on how well he or she is performing the breathing and how his or her heart rate signal patterns (via RRi) are responding. The breathing pace may not change based on this feedback, but the user may be informed on how well he or she is doing so the user has feedback to know if he or she needs to adjust, or just to get a sense of where he or she is at in practice compared to other sessions (is the user improving, is the user having an off day, etc.).

Optimization of a Mechanical System to Protect Against Elemental Impact while Allowing for Mass Customization of a Wearable Device A wearable device that may be positioned at some location on the user's body, for example wrist, ear, chest, neck or otherwise, can utilize multiple onboard sensors to collect information on the user. The environment that the device operates in a high external stress environment that is subject to elemental stressors such as human sweat, body lotions, water, dust, etc. This extreme environment results in the devices having to be designed in such a way that they are robust, with the trade-off being the ability to customize the designs.

The mechanical structure employed in some embodiments allows for a specialized environmentally sealed module to be inserted into various structures without the need to redesign and revalidate the device's sensor functions.

Figure 15:
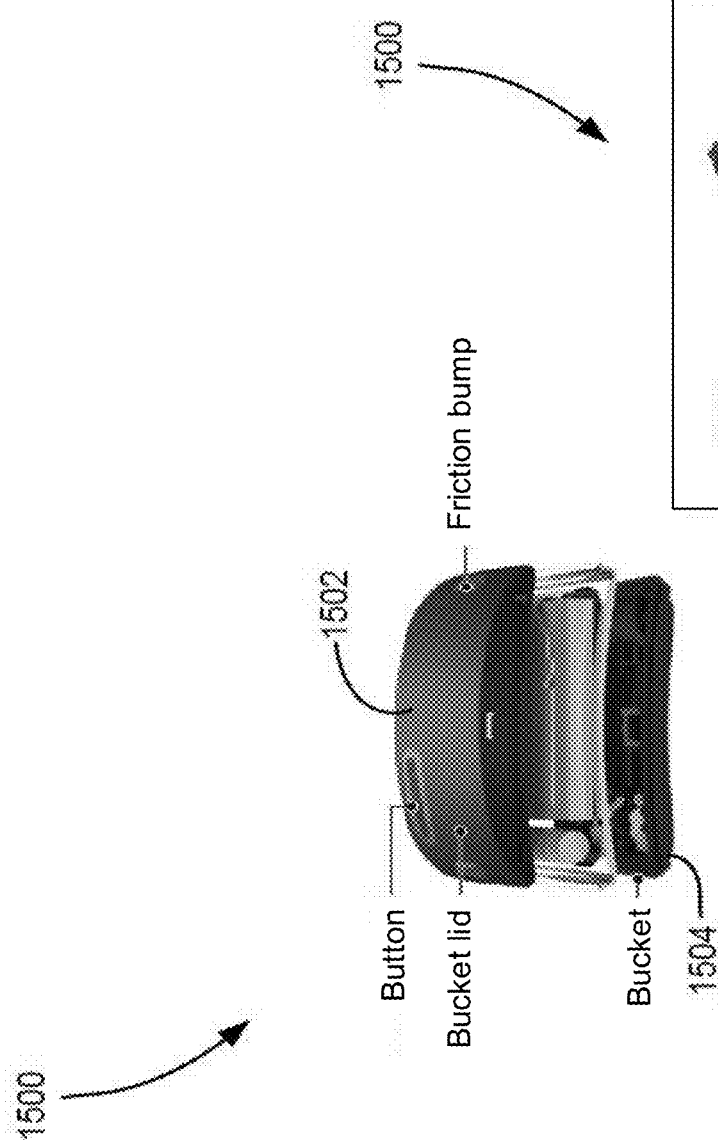
FIGS. 15 and 16 illustrate an environmentally sealed module which may be used in a wearable device in accordance with one embodiment.
Figure 16:
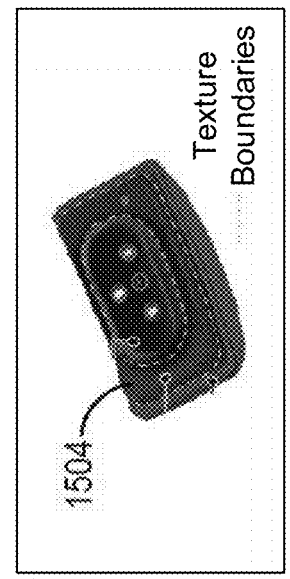

FIGS. 15 and 16 illustrate one potential implementation of this design. Particularly, FIGS. 15 and 16 depict an environmentally sealed module 1500 which may be used in a wearable device in accordance with one embodiment. As an option, the present module 1500 may be implemented in conjunction with features from any other embodiment listed herein, such as those described with reference to the other FIGS. Of course, however, such module 1500 and others presented herein may be used in various applications and/or in permutations which may or may not be specifically described in the illustrative embodiments listed herein. Further, the module 1500 presented herein may be used in any desired environment.

The environmentally sealed module 1500 is made up of an upper "bucket lid" 1502 and a lower "bucket" 1504. Once combined for the purposes of this document the sealed enclosure is then simply referred to as the bucket.

The bucket may be made of a hard plastic material such as a polycarbonate and/or a soft material such as a thermoplastic. The top and bottom sections (bucket lid and bucket) may be joined together utilizing a resin and/or adhesive material, ultrasonically welded, thermally bonded, or a combination of these methods, to ensure that the electrical components encapsulated inside the bucket are completely sealed off from the surrounding environment.

The bucket may have other types of materials bonded to it as well to facilitate various other primary or non-primary functions of the completed device. For example, an insert of molded or co-molded thermoplastic material may be bonded to the device to allow for motion actions such as the pressing of a button. This may also include the bonding of an in mold decoration (IMD) which is preferably water clear in form to allow for optical signals to pass back and forth between the internal and external environments around the bucket. The concept, however, is to ensure that no matter what sort of additional features and/or bonding elements are added to the bucket the bucket's environmental envelope remains intact.

After the primary function of the bucket is achieved (maintaining environmental isolation) secondary functions are enabled. An example of a secondary enablement is the ability to utilize mass customization techniques whereby the universal bucket design allows for the changing of external cosmetic parameters such as stainless steel housings, real or simulated leather bands, silicone or thermoplastic straps or housings for mounting to various points on the users' bodies, etc.

The description herein is presented to enable any person skilled in the art to make and use the invention and is provided in the context of particular applications of the invention and their requirements. Various modifications to the disclosed embodiments will be readily apparent to those skilled in the art and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

In particular, various embodiments of the invention discussed herein are implemented using the Internet as a means of communicating among a plurality of computer systems. One skilled in the art will recognize that the present invention is not limited to the use of the Internet as a communication medium and that alternative methods of the invention may accommodate the use of a private intranet, a Local Area Network (LAN), a Wide Area Network (WAN) or other means of communication. In addition, various combinations of wired, wireless (e.g., radio frequency) and optical communication links may be utilized.

The program environment in which one embodiment of the invention may be executed illustratively incorporates one or more general-purpose computers or special-purpose devices such hand-held computers. Details of such devices (e.g., processor, memory, data storage, input and output devices) are well known and are omitted for the sake of clarity.

It should also be understood that the techniques of the present invention might be implemented using a variety of technologies. For example, the methods described herein may be implemented in software running on a computer system, or implemented in hardware utilizing one or more processors and logic (hardware and/or software) for performing operations of the method, application specific integrated circuits, programmable logic devices such as Field Programmable Gate Arrays (FPGAs), and/or various combinations thereof. In one illustrative approach, methods described herein may be implemented by a series of computer-executable instructions residing on a storage medium such as a physical (e.g., non-transitory) computer-readable medium. In addition, although specific embodiments of the invention may employ object-oriented software programming concepts, the invention is not so limited and is easily adapted to employ other forms of directing the operation of a computer.

The invention can also be provided in the form of a computer program product comprising a computer readable storage or signal medium having computer code thereon, which may be executed by a computing device (e.g., a processor) and/or system. A computer readable storage medium can include any medium capable of storing computer code thereon for use by a computing device or system, including optical media such as read only and writeable CD and DVD, magnetic memory or medium (e.g., hard disk drive, tape), semiconductor memory (e.g., FLASH memory and other portable memory cards, etc.), firmware encoded in a chip, etc.

A computer readable signal medium is one that does not fit within the aforementioned storage medium class. For example, illustrative computer readable signal media communicate or otherwise transfer transitory signals within a system, between systems e.g., via a physical or virtual network, etc.

Figure 17:
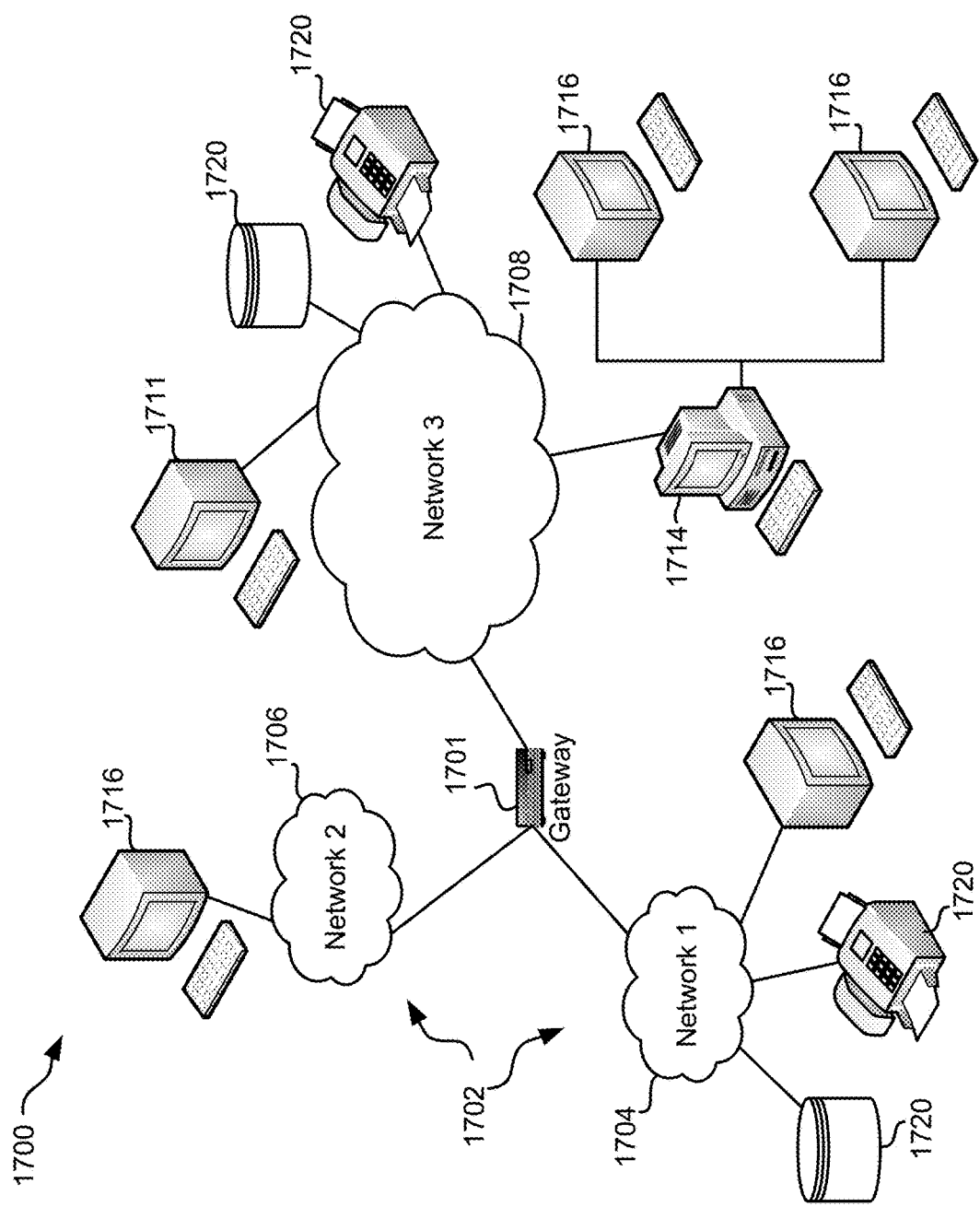
FIG. 17 illustrates an architecture, in accordance with one embodiment.

FIG. 17 illustrates an architecture 1700, in accordance with one embodiment. As an option, the present architecture 1700 may be implemented in conjunction with features from any other embodiment listed herein, such as those described with reference to the other FIGS. Of course, however, such architecture 1700 and others presented herein may be used in various applications and/or in permutations which may or may not be specifically described in the illustrative embodiments listed herein. Further, the architecture 1700 presented herein may be used in any desired environment.

As shown in FIG. 17, a plurality of remote networks 1702 are provided including a first remote network 1704 and a second remote network 1706. A gateway 1701 may be coupled between the remote networks 1702 and a proximate network 1708. In the context of the present network architecture 1700, the networks 1704, 1706 may each take any form including, but not limited to a LAN, a WAN such as the Internet, public switched telephone network (PSTN), internal telephone network, etc.

In use, the gateway 1701 serves as an entrance point from the remote networks 1702 to the proximate network 1708. As such, the gateway 1701 may function as a router, which is capable of directing a given packet of data that arrives at the gateway 1701, and a switch, which furnishes the actual path in and out of the gateway 1701 for a given packet.

Further included is at least one data server 1714 coupled to the proximate network 1708, and which is accessible from the remote networks 1702 via the gateway 1701. It should be noted that the data server(s) 1714 may include any type of computing device/groupware. Coupled to each data server 1714 is a plurality of user devices 1716. Such user devices 1716 may include a desktop computer, laptop computer, hand-held computer, printer or any other type of logic. It should be noted that a user device 1711 may also be directly coupled to any of the networks, in one embodiment.

A peripheral 1720 or series of peripherals 1720, e.g. facsimile machines, printers, networked storage units, etc., may be coupled to one or more of the networks 1704, 1706, 1708. It should be noted that databases, servers, and/or additional components may be utilized with, or integrated into, any type of network element coupled to the networks 1704, 1706, 1708. In the context of the present description, a network element may refer to any component of a network.

According to some approaches, methods and systems described herein may be implemented with and/or on virtual systems and/or systems which emulate one or more other systems, such as a UNIX system which emulates a MAC OS environment, a UNIX system which virtually hosts a MICROSOFT WINDOWS environment, a MICROSOFT WINDOWS system which emulates a MAC OS environment, etc. This virtualization and/or emulation may be enhanced through the use of VMWARE software, in some embodiments.

In more approaches, one or more networks 1704, 1706, 1708, may represent a cluster of systems commonly referred to as a "cloud." In cloud computing, shared resources, such as processing power, peripherals, software, data processing and/or storage, servers, etc., are provided to any system in the cloud, preferably in an on-demand relationship, thereby allowing access and distribution of services across many computing systems. Cloud computing typically involves an Internet or other high speed connection (e.g., 4G LTE, fiber optic, etc.) between the systems operating in the cloud, but other techniques of connecting the systems may also be used.

Figure 18:
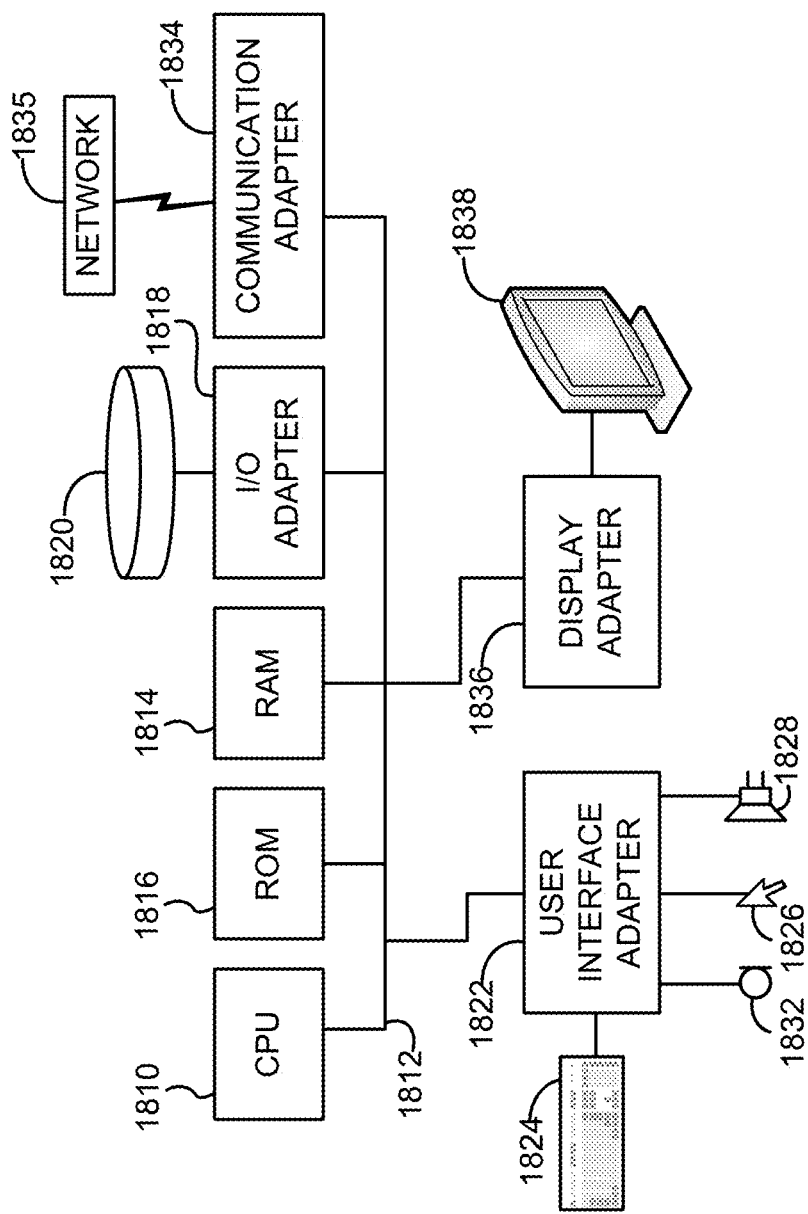
FIG. 18 shows a representative hardware environment associated with a user device and/or server of FIG. 17, in accordance with one embodiment.

FIG. 18 shows a representative hardware environment associated with a user device 1716 and/or server 1714 of FIG. 17, in accordance with one embodiment. Such figure illustrates a typical hardware configuration of a workstation having a central processing unit 1810, such as a microprocessor, and a number of other units interconnected via a system bus 1812.

The workstation shown in FIG. 18 includes a Random Access Memory (RAM) 1814, Read Only Memory (ROM) 1816, an I/O adapter 1818 for connecting peripheral devices such as disk storage units 1820 to the bus 1812, a user interface adapter 1822 for connecting a keyboard 1824, a mouse 1826, a speaker 1828, a microphone 1832, and/or other user interface devices such as a touch screen and a digital camera (not shown) to the bus 1812, communication adapter 1834 for connecting the workstation to a communication network 1835 (e.g., a data processing network) and a display adapter 1836 for connecting the bus 1812 to a display device 1838.

The workstation may have resident thereon an operating system such as the Microsoft WINDOWS Operating System (OS), a MAC OS, a UNIX OS, etc. It will be appreciated that a preferred embodiment may also be implemented on platforms and operating systems other than those mentioned. A preferred embodiment may be written using JAVA, XML, C, and/or C++ language, or other programming languages, along with an object oriented programming methodology. Object oriented programming (OOP), which has become increasingly used to develop complex applications, may be used.

Moreover, a system according to various embodiments may include a processor and logic integrated with and/or executable by the processor, the logic being configured to perform one or more of the process steps recited herein. By integrated with, what is meant is that the processor has logic embedded therewith as hardware logic, such as an application specific integrated circuit (ASIC), a FPGA, etc. By executable by the processor, what is meant is that the logic is hardware logic; software logic such as firmware, part of an operating system, part of an application program; etc., or some combination of hardware and software logic that is accessible by the processor and configured to cause the processor to perform some functionality upon execution by the processor. Software logic may be stored on local and/or remote memory of any memory type, as known in the art. Any processor known in the art may be used, such as a software processor module and/or a hardware processor such as an ASIC, a FPGA, a central processing unit (CPU), an integrated circuit (IC), a graphics processing unit (GPU), etc.

The inventive concepts disclosed herein have been presented by way of example to illustrate the myriad features thereof in a plurality of illustrative scenarios, embodiments, and/or implementations. It should be appreciated that the concepts generally disclosed are to be considered as modular, and may be implemented in any combination, permutation, or synthesis thereof. In addition, any modification, alteration, or equivalent of the presently disclosed features, functions, and concepts that would be appreciated by a person having ordinary skill in the art upon reading the instant descriptions should also be considered within the scope of this disclosure.

While various embodiments have been described above, it should be understood that they have been presented by way of example only, and not limitation. Thus, the breadth and scope of an embodiment of the present invention should not be limited by any of the above-described exemplary embodiments, but should be defined only in accordance with the following claims and their equivalents.

What is claimed is:

1. A method for predictively controlling an operational state of a wearable device, the method comprising:
   collecting historical sensor data acquired by one or more sensors of a wearable device;
   in response to a determination that at least some of the historical sensor data is inaccurate, correcting the inaccurate historical sensor data, wherein the inaccurate historical sensor data is corrected using predefined spectral analysis algorithms,
   analyzing the historical sensor data for detecting a pattern therein, wherein the analyzed historical sensor data includes only accurate historical sensor data and/or corrected historical sensor data; and
   instructing change of the operational state at a time that is determined based on the detected pattern.

2. The method as recited in claim 1, comprising outputting an alert for a user of the wearable device.

3. The method as recited in claim 1, wherein the historical sensor data includes biometric data.

4. A computer program product for predictively controlling an operational state of a wearable device, the computer program product comprising a nontransitory computer readable medium having program instructions embodied therewith, the program instructions executable by a computer to cause the computer to:
   collect historical heartrate sensor data acquired by one or more sensors of a wearable device;
   analyze the historical heartrate sensor data for detecting a pattern therein;
   in response to detecting a pattern, predict a time to change an operational state of the wearable device based on the detected pattern,
   wherein the pattern is based on the collected historical heartrate sensor data having a predefined degree of similarity with previously analyzed historical heartrate sensor data,
   wherein the predicted time to change the operational state of the wearable device is based on both timestamp information of the collected historical heartrate sensor data and timestamp information of the previously analyzed historical heartrate sensor data; and
   instruct change of the operational state at the predicted time.

5. A system, comprising:
   a processor; and
   logic integrated with the processor, executable by the processor, or integrated with and executable by the processor, the logic being configured to:
   collect historical sensor data acquired by one or more sensors of a wearable device;
   in response to a determination that at least some of the historical sensor data is inaccurate, instructing the device to acquire resonance breathing sensor data;
   collecting the resonance breathing sensor data;
   analyze the historical sensor data and the resonance breathing sensor data for detecting a pattern therein; and
   instruct change of an operational state of the wearable device at a time that is determined based on the detected pattern.

6. The system as recited in claim 5, comprising logic for outputting an alert for a user of the wearable device.

7. The system as recited in claim 5, wherein the historical sensor data includes biometric data.

8. The method as recited in claim 1,
wherein internal algorithm parameters are utilized for analyzing the historical sensor data, and comprising:
determining whether at least some predetermined conditions are met, wherein a first of the at least some predefined conditions includes a battery of the wearable device containing less than a predetermined amount of charge; and
in response to a determination that the first of the at least some predefined conditions is met, instructing adjustment of the internal algorithm parameters.

9. The method as recited in claim 8, wherein the instruction for adjustment of the internal algorithm parameters includes a sub-instruction to utilize a different runtime operation code than a currently utilized runtime operation code, wherein the different runtime operation code is configured to cause a decrease in sample rate of the sensor of the wearable device and as a result increase power efficiency.

10. The method as recited in claim 9, wherein the historical sensor data consists of heartrate data.

11. The method as recited in claim 1, wherein the predefined spectral analysis algorithms utilize least-square principles.

12. The computer program product as recited in claim 4, wherein the predicted time to change the operational state of the wearable device is prior to a time at which an event is expected to occur.

13. The computer program product as recited in claim 12, wherein the event is a regularly scheduled event, and comprising program instructions for causing the computer to instruct the wearable device to output a prompt for a user of the wearable device to engage in the regularly scheduled event.

14. The computer program product as recited in claim 12, wherein the event is a regularly scheduled event, and comprising program instructions for causing the computer to instruct the wearable device to output an alert of the expected event.

15. The system as recited in claim 5,
wherein analyzing the historical sensor data includes implementing a machine learning algorithm,
wherein the determined time to change the operational state of the wearable device is prior to a time at which an event is expected to occur,
wherein the event that is expected to occur is a regularly scheduled event according to results of implementing the machine learning algorithm,
wherein the regularly scheduled event is determined based on, and comprising logic for:
instructing the wearable device to output a prompt for a user of the wearable device to engage in the regularly scheduled event; and
instructing the wearable device to output an alert of the expected event.

\* \* \* \* \*